US012186086B2

(12) United States Patent
Yu et al.

(10) Patent No.: US 12,186,086 B2
(45) Date of Patent: *Jan. 7, 2025

(54) SYSTEMS AND METHODS FOR REDUCED LEAD ELECTROCARDIOGRAM DIAGNOSIS USING DEEP NEURAL NETWORKS AND RULE-BASED SYSTEMS

(71) Applicant: GE Precision Healthcare LLC, Wauwatosa, WI (US)

(72) Inventors: Long Yu, Wauwatosa, WI (US); Joel Qiuzhen Xue, Wauwatosa, WI (US); Gordon Ian Rowlandson, Wauwatosa, WI (US)

(73) Assignee: GE Precision Healthcare LLC, Wauwatosa, WI (US)

( * ) Notice: Subject to any disclaimer, the term of this patent is extended or adjusted under 35 U.S.C. 154(b) by 41 days.

This patent is subject to a terminal disclaimer.

(21) Appl. No.: 18/091,064

(22) Filed: Dec. 29, 2022

(65) Prior Publication Data
US 2023/0143594 A1 May 11, 2023

Related U.S. Application Data

(63) Continuation of application No. 16/596,640, filed on Oct. 8, 2019, now Pat. No. 11,617,528.

(51) Int. Cl.
| A61B 5/282 | (2021.01) |
| A61B 5/00 | (2006.01) |
| A61B 5/339 | (2021.01) |
| G06N 3/042 | (2023.01) |
| G06N 3/08 | (2023.01) |
| G16H 50/20 | (2018.01) |

(52) U.S. Cl.
CPC .............. *A61B 5/282* (2021.01); *A61B 5/339* (2021.01); *A61B 5/7221* (2013.01); *A61B 5/7267* (2013.01); *G06N 3/042* (2023.01); *G06N 3/08* (2013.01); *G16H 50/20* (2018.01)

(58) Field of Classification Search
CPC ................................ A61B 5/282; A61B 5/339
USPC ........................................................ 600/523
See application file for complete search history.

(56) References Cited

U.S. PATENT DOCUMENTS

| 2003/0028119 A1* | 2/2003 | Xue ........................ A61B 5/339 |
| | | 600/523 |
| 2009/0177106 A1* | 7/2009 | Ricke ...................... A61B 5/349 |
| | | 600/523 |

(Continued)

*Primary Examiner* — Nicole F Lavert

(57) ABSTRACT

Methods and systems are provided for automatically diagnosing a patient based on a reduced lead electrocardiogram (ECG), using one or more deep neural networks. In one embodiment, a method for automatically diagnosing a patient using a reduced lead ECG comprises, acquiring reduced lead ECG data, wherein the reduced lead ECG data comprises less than twelve lead signals, determining a type of each of the less than twelve lead signals, selecting a deep neural network based on the type of each of the less than twelve lead signals, and mapping the less than twelve lead signals to a diagnosis using the deep neural network. In this way, reduced lead ECG data may be mapped to a diagnosis using an intelligently selected deep neural network, wherein the deep neural network was trained on reduced lead ECG data comprising a same set of ECG lead types as the acquired reduced lead ECG data.

20 Claims, 13 Drawing Sheets

(56) References Cited

U.S. PATENT DOCUMENTS

2014/0194760 A1\* 7/2014 Albert ................ A61B 5/339
                                                600/509
2018/0116597 A1\* 5/2018 Yu .................... A61B 5/0064

\* cited by examiner

SYSTEMS AND METHODS FOR REDUCED LEAD ELECTROCARDIOGRAM DIAGNOSIS USING DEEP NEURAL NETWORKS AND RULE-BASED SYSTEMS

CROSS-REFERENCE TO RELATED APPLICATIONS

This application is based on and claims priority under 35 U.S.C. § 119 to U.S. patent application Ser. No. 16/596,640 filed on Oct. 8, 2019, in the U.S. Patent & Trademark Office, the disclosure of which is incorporated by reference herein in its entirety.

TECHNICAL FIELD

Embodiments of the subject matter disclosed herein relate to the analysis of electrocardiograms (ECGs), and more specifically, to methods and systems for automatically diagnosing ECGs using deep neural networks and rule-based systems.

BACKGROUND

Heart disease has become the most common disease that affects humans worldwide. Each year millions of people die from heart attacks and an equal number undergo coronary artery bypass surgery or balloon angioplasty for advanced heart disease. Early detection and timely treatment may reduce the probability and/or severity of such events. Early detection may improve the quality of life and slow the progression of heart failure. Recording an electrocardiogram (ECG) is a non-invasive approach used to assess a patient's heart condition, which may enable early detection of cardiac irregularities. The features of the ECG may lead to a relatively accurate and fast diagnosis.

ECGs may provide information on the normal and/or pathological physiology of the heart. Conventionally, twelve leads are measured using ten electrodes placed in contact with a patient's skin. The twelve leads provide information on the electrical potential through the heart along twelve distinct axes intersecting the heart, and the variation in strength of these electrical potentials in time provides twelve distinct, semi-periodic signals. These twelve signals may then be used to assess the state of the heart, and potentially diagnose one or more cardiac conditions, such as arrhythmias, cardiac infarctions, cardiac hypertrophy, etc.

However, in some cases, it may be desired to assess the physiological state of a patient's heart using less than the conventional twelve leads. Collection of twelve lead signals relies on placement of six electrodes on the chest of a patient, and one electrode on each of the patient's four limbs. However, in some cases, placement of each of the ten electrodes on the patient may be undesirable. For example, post-surgery, a patient may have bandages or stitches over a limb or the chest, inhibiting electrode placement. In another example, it may be difficult to place each of the six chest electrodes on a neonate, as the chest area may be relatively small compared to the size of an adult patient, or uncomfortable/irritating for the neonate. In these cases, it is desired to monitor the state of a patient's heart using less than the conventional twelve leads.

Conventional diagnostic approaches/algorithms may rely on twelve lead ECGs, and may produce inconsistent diagnosis, or may be unable to determine a diagnosis, when applied to reduced lead ECGs (as used herein, reduced lead ECGs will be understood to comprise ECGs having from one to eleven leads/signals of the conventional twelve). One attempt to apply conventional diagnostic approaches to reduced lead ECGs comprises expanding the reduced lead ECGs to the conventional twelve lead signals by simulating the one or more missing lead signals, thereby mimicking a conventional full ECG (as used herein, a full ECG refers to a conventional twelve lead ECG). The conventional diagnostic approach may then be applied to the simulated, full ECG.

However, the inventors herein have identified issues with the above approach. For example, simulated ECG leads may have varying degrees of accuracy, and may therefore produce inconsistent results when used to diagnose a heart with the criteria built from a conventional twelve lead ECG. Further, simulating ECG leads may consume substantial computational resources. Thus, exploring techniques for increasing diagnostic accuracy of ECG diagnostic systems for use on reduced lead ECG data, while reducing reliance on ECG lead simulation, is generally desired.

SUMMARY

The present disclosure at least partially addresses the issues described above. In one embodiment, a diagnosis may be generated for a reduced lead ECG, without simulating missing leads, by a method comprising, acquiring reduced lead ECG data, wherein the reduced lead ECG data comprises less than twelve lead signals, determining a type of each of the less than twelve lead signals, selecting a deep neural network based on the type of each of the less than twelve lead signals, and mapping the less than twelve lead signals to a diagnosis using the deep neural network. In this way, a diagnosis for reduced lead ECG data may be determined without simulating the one or more missing lead signals, by intelligently selecting a deep neural network trained on reduced lead ECG data comprising the same types of ECG leads as the acquired reduced ECG data.

The above advantages and other advantages, and features of the present description will be readily apparent from the following Detailed Description when taken alone or in connection with the accompanying drawings. It should be understood that the summary above is provided to introduce in simplified form a selection of concepts that are further described in the detailed description. It is not meant to identify key or essential features of the claimed subject matter, the scope of which is defined uniquely by the claims that follow the detailed description. Furthermore, the claimed subject matter is not limited to implementations that solve any disadvantages noted above or in any part of this disclosure.

BRIEF DESCRIPTION OF THE DRAWINGS

Various aspects of this disclosure may be better understood upon reading the following detailed description and upon reference to the drawings in which.

Figure 1:
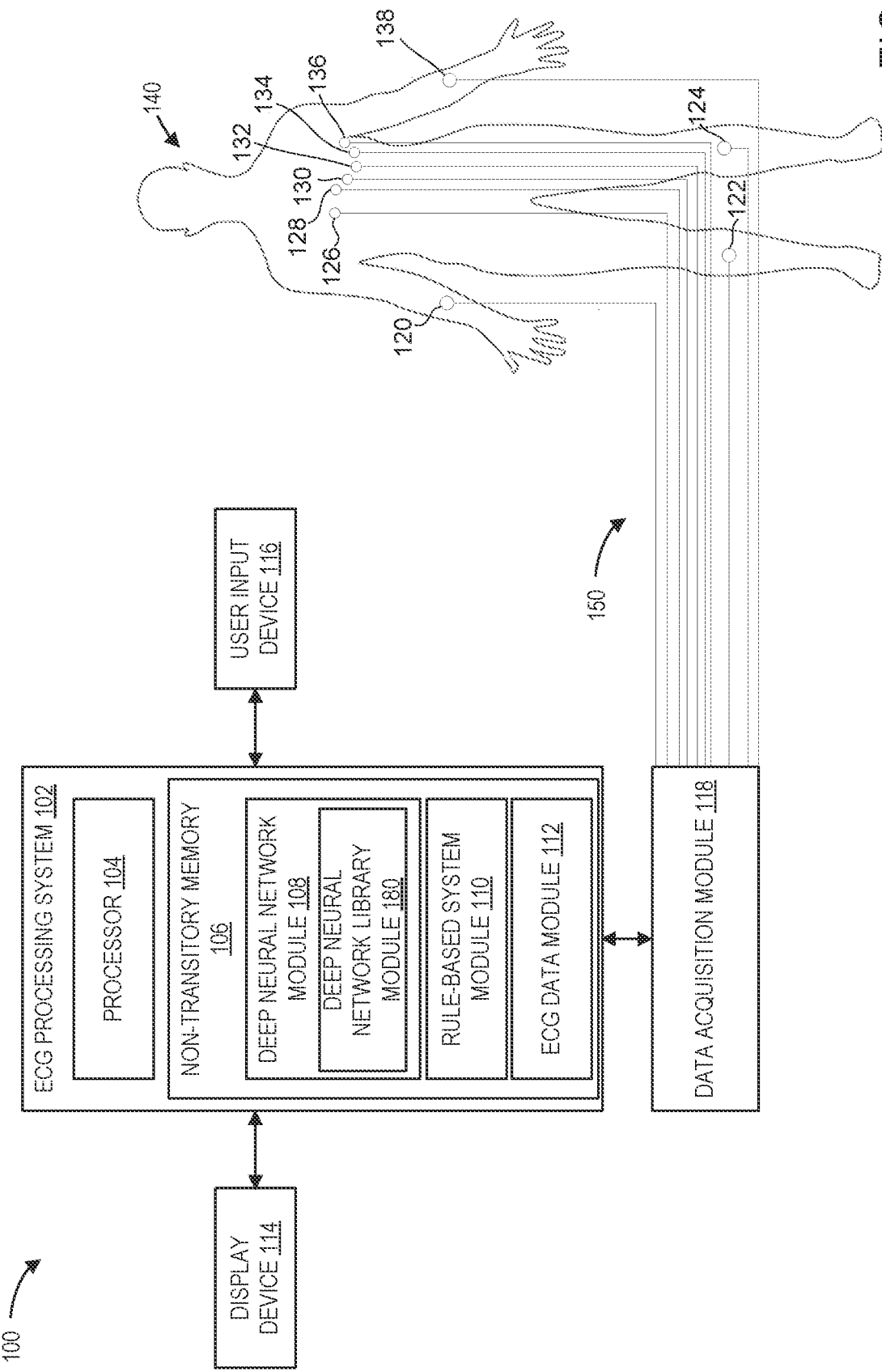
FIG. 1 shows a block diagram of an exemplary embodiment of an ECG system.

The drawings illustrate specific aspects of the described systems and methods for automatically diagnosing reduced lead ECG data using a reduced lead ECG diagnostic system. Together with the following description, the drawings demonstrate and explain the structures, methods, and principles described herein. In the drawings, the size of components may be exaggerated or otherwise modified for clarity. Well-known structures, materials, or operations are not shown or described in detail to avoid obscuring aspects of the described components, systems and methods.

DETAILED DESCRIPTION

The following description relates to systems and methods for automatically diagnosing electrocardiograms (ECGs) using a hybrid system comprising one or more deep neural networks, and a rule-based system, such as the rule-based system described in Rawi, Atiaf Ayal, and Muzhir Shaban Al-Ani. "A rule-based expert system for automated ECG diagnosis." International Journal of Advances in Engineering & Technology 6.4 (2013): 1480, the entire contents of which are hereby incorporated by reference for all purposes. In particular, the following description relates to systems and methods for increasing the adaptability and accuracy of ECG diagnostic systems by combining one or more deep neural networks with a rule-based system to produce a hybrid system with increased diagnostic accuracy, and increased adaptability to particular use-cases. The hybrid system may further enable accurate diagnosis of reduced lead ECG data by learning to directly map features of reduced lead ECG data to diagnoses, bypassing the need to simulate missing lead signals.

In some embodiments, ECG data may be acquired from a patient via an electrocardiograph (ECG), such as ECG system 100, shown in FIG. 1. The ECG data acquired thereby may be automatically diagnosed by ECG processing system 102, implementing one or more hybrid ECG diagnostic systems, such as one or more hybrid ECG diagnostic systems 200, 300, and 400, shown in FIG. 2, FIG. 3, and FIG. 4, respectively. The ECG processing system 102 may implement the one or more hybrid ECG diagnostic systems to diagnose ECG data by executing one or more operations of method 500, shown in FIG. 5, method 600 shown in FIG. 6, method 700 shown in FIG. 7, and/or method 800 shown in FIG. 8. In a first embodiment, ECG processing system 102 may implement hybrid ECG diagnostic system 200 to automatically diagnose acquired ECG data using one or more operations of method 600, shown in FIG. 6. In a second embodiment, ECG processing system 102 may implement hybrid ECG diagnostic system 300 to automatically diagnose acquired ECG data using one or more operations of method 700, shown in FIG. 7. In a third embodiment, ECG processing system 102 may implement hybrid ECG diagnostic system 400 to automatically diagnose acquired ECG data using one or more operations of method 800, shown in FIG. 8. FIG. 10 shows one embodiment of a twelve lead ECG which may be automatically diagnosed using the above systems and methods, along with a first, incorrect diagnosis produced using a rule-based system alone, and a second, correct diagnosis, produced using a hybrid ECG diagnostic system according to an embodiment of the current disclosure. Hybrid ECG diagnostic systems 200, 300, and 400 may be trained according to method 900 shown in FIG. 9, thereby enabling the hybrid ECG diagnostic systems to adapt to particular use cases by training on use case specific data.

Figure 11:
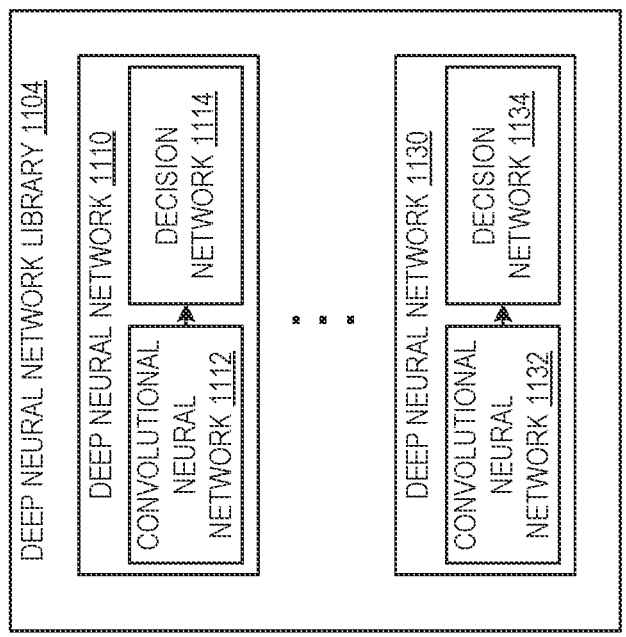
FIG. 11 is a schematic diagram illustrating a reduced lead ECG diagnostic system, according to an exemplary embodiment.

Further, the current disclosure provides for automatically diagnosing reduced lead ECGs by selecting a deep neural network, such as deep neural network 1110, from a deep neural network library, such as deep neural network library 1104 shown in FIG. 11. The selected deep neural network 1110 may comprise a deep neural network trained on reduced lead ECG data and may be used in hybrid ECG diagnostic system 200 shown in FIG. 2, hybrid ECG diagnostic system 300 shown in FIG. 3, and/or hybrid ECG diagnostic system 400 shown in FIG. 4, to diagnose reduced lead ECG data by executing one or more operations of method 1300 shown in FIG. 13. The deep neural network library 1104 may comprise a plurality of distinct deep learning networks, each trained using a different reduced lead set, according to method 1200 shown in FIG. 12. In one embodiment, a first trained deep neural network in deep neural network library 1104 may comprise parameters learned via training on reduced lead ECG data, wherein the reduced lead ECG data comprises lead types I, II, III, a VR, aVL and aVF (the limb leads), but is missing lead types V1, V2, V3, V4, V5, and V6 (the chest leads), thus the first trained deep neural network may be selected from deep neural network library 1104 to map acquired reduced lead ECG data to a diagnosis, wherein the acquired reduced lead ECG data comprises the same lead types (leads I, II, III, aVR, aVL, and aVF) on which the first trained deep neural network was trained. In other words, by training a plurality of deep neural networks using different permutations of reduced lead sets (wherein 4,094 different reduced lead set permutations exist for a conventional twelve lead ECG), storing the trained deep neural networks in a deep neural network library according to the reduced lead ECG data on which the deep neural networks were trained, acquired ECG data with one or more missing leads may be efficiently and accurately mapped to a diagnosis by selecting a deep neural network from the deep neural network library trained on reduced lead ECG data missing the same type(s) of lead(s) as the acquired data.

As used herein, lead type (also referred to as ECG lead type) refers to one of the twelve or fifteen conventionally measured ECG leads (I, II, III, aVR, aVL, aVF, V1, V2, V3, V4, V5, V6, V7, V8, and V9). In other words, a conventional twelve or 15 lead ECG comprises one signal/lead of each of the twelve or 15 distinct lead types. The term lead type is used to differentiate ECG measurements taken along a specific axis through the heart (a lead type), from specific instances of ECG measurements (leads). For example, a training data set may comprise thousands of distinct ECG leads (for example, from thousands of different patients, or from a few hundred patients with repeated measurements), but the training data set may comprise just six lead types, for example, V1, V2, V3, V4, V5, and V6. That is, each of the thousands of leads in the training data set is of type V1, V2, V3, V4, V5, or V6, and none of the leads in the training data set are of type I, II, III, aVR, aVL, or aVF.

Further, as used herein, a full lead set, a full set of ECG leads, a full twelve lead ECG, a full ECG, and other similar terms, refer to an electrocardiogram comprising twelve distinct leads, one of each of the twelve lead types. For example, an ECG taken of a patient comprising a type I lead, a type II lead, a type III lead, a type aVR lead, a type aVL lead, a type aVF lead, a type V1 lead, a type V2 lead, a type V3 lead, a type V4 lead, a type V5 lead, and a type V6 lead, may be referred to as a full ECG, a twelve lead ECG, a full twelve lead ECG, etc. Conversely, the terms reduced lead set, reduced lead ECG data, reduced lead data, reduced ECG lead set, and other similar terms, will be understood to refer to an ECG comprising no more than eleven, and no less than one, lead(s), each of a distinct lead type.

The term preliminary diagnosis, as used herein, shall be understood to refer to a diagnosis or diagnostic prediction of a deep neural network, or rule-based system, which is not utilized as a final diagnosis as such, but is input into one or more additional deep neural networks/rule-based systems to provide the one or more additional deep neural networks/ rule-based systems with additional information, thereby facilitating more accurate prediction of a final diagnosis (the term final diagnosis and diagnosis are herein used interchangeably). In other words, a preliminary diagnosis may be generated by a hybrid system for internal use within the hybrid system, whereas a diagnosis (also referred to as a final diagnosis) may be output to a user, such as via a display device, or transmitted to one or more client devices.

As used herein, a final diagnosis, an ECG diagnosis, a diagnosis, and other similar terms, will be understood to comprise an assessment of the normality and/or abnormality of one or more features of an ECG. Specifically, an ECG diagnosis may comprise an evaluation of one or more deviations of an acquired ECG from a "baseline" or "healthy" ECG, and may indicate one or more types of arrhythmias, and may further indicate one or more expected causes underlying the one or more types of arrhythmias. In some embodiments, a diagnosis may comprise a feature by feature evaluation of an ECG, with an indication of how/if each feature deviates from a baseline ECG (e.g., normal sinus rhythm, QRS widening, repolarization abnormality, rightward axis, left bundle branch block, etc.).

Referring to FIG. 1, an electrocardiograph (ECG) system 100 is shown, in accordance with an exemplary embodiment. ECG system 100 comprises a set of electrodes 150, attached to a patient 140. Electrodes 150 are electrically coupled to data acquisition module 118, thus enabling data acquisition module 118 to measure ECG waveform data by determining a difference in electrical potential between two or more electrodes of electrodes 150. Data acquisition module 118 is communicatively coupled to ECG processing system 102, for processing, storing, and/or diagnosing, ECG data acquired by data acquisition module 118. ECG processing system 102 is further communicatively coupled to a display device 114, which is configured to display ECG data and/or diagnoses determined for the ECG data, as well as user input device 116, which may enable a user to enter data into ECG processing system 102 or interact with data within non-transitory memory 106. Further, ECG system 100 may be communicatively coupled to one or more client devices (not shown), such as through a network connection, or through the Internet.

Data acquisition module 118 is configured to acquire time traces of electrical potentials between two or more electrodes of electrodes 150. In ECG system 100, electrodes 150 comprise ten electrodes, configured to measure a twelve lead ECG. In some embodiments, ECG system 100 may comprise 13 electrodes and may be configured to acquire fifteen lead ECG data. Although the meaning of a twelve lead ECG will be well understood by a person having ordinary skill in the art, briefly, a twelve lead ECG comprises a record of the electrical potential of the heart, as a function of time, measured along twelve distinct axes intersecting the heart. Therefore, a twelve lead ECG comprises twelve distinct, time varying signals, wherein each of the twelve distinct time varying signals represents the electrical activity of the heart measured along a different axis. The electrodes 150 may include an electrically conductive gel that contacts the patient's skin and conducts to the electrode electrical signals that are present at the skin. The patient 140's heart produces an electrical signal that is referred to as an ECG waveform, and which may also be referred to herein as an ECG signal, an ECG lead signal, an ECG, or ECG data.

Specifically, electrodes 150 include four limb electrodes, including electrode 120 placed on a right arm of patient 140 (and therefore conventionally referred to as RA), electrode 122 placed on a right leg of patient 140 (and therefore conventionally referred to as RL), electrode 138 placed on a left arm of patient 140 (and therefore conventionally referred to as LA), and electrode 124 placed on a left leg of patient 140 (and therefore conventionally referred to as LL). The four limb electrodes may be used to measure the electrical potential of the heart along six distinct axes intersecting the heart, where each of the electrical potentials measured along a distinct axis is referred to as a lead. The six leads which the four limb electrodes are configured to measure are referred to as I (which comprises the electrical potential difference between electrode 138 and electrode 120), II (which comprises the electrical potential difference between electrode 124 and electrode 120), III (which comprises the electrical potential difference between electrode 124 and electrode 138), aVR (which comprises the electrical potential difference between electrode 120 and the average of electrodes 124 and 138), aVL (which comprises the electrical potential difference between electrode 138 and the average of electrodes 120 and 124), and aVF (which comprises the electrical potential difference between electrode 124 and the average of electrodes 120 and 138).

Further, electrodes 150 comprise six chest electrodes, including electrode 126 (conventionally referred to as V1), electrode 128 (conventionally referred to as V2), electrode 130 (conventionally referred to as V3), electrode 132 (conventionally referred to as V4), electrode 134 (conventionally referred to as V5), and electrode 136 (conventionally referred to as V6). The six chest electrodes, in conjunction with the limb electrodes, are configured to measure electrical potentials through six distinct axes intersecting the heart in a horizontal plane (that is, a plane perpendicular to the plane in which the six limb leads are measured). Specifically, the six leads which the six chest electrodes are configured to measure are referred to as V1 (which comprises the potential difference between electrode 126 and the average of electrodes 120, 124, and 138), V2 (which comprises the potential difference between electrode 128 and the average of electrodes 120, 124, and 138), V3 (which comprises the potential difference between electrode 130 and the average of electrodes 120, 124, and 138), V4 (which comprises the potential difference between electrode 132 and the average of electrodes 120, 124, and 138), V5 (which comprises the potential difference between electrode 134 and the average of electrodes 120, 124, and 138), and V6 (which comprises the potential difference between electrode 136 and the average of electrodes 120, 124, and 138).

Although ECG system 100 comprises ten electrodes and is configured to measure a full twelve lead ECG, it will be appreciated that the current disclosure provides for ECG systems comprising more or less than ten electrodes, and/or ECGs comprising more or less than twelve leads. The current disclosure also provides for electrode placement other than that described above with reference to electrodes 120-138. In particular, portions of the disclosure are directed towards increased diagnostic accuracy using reduced ECG lead sets, which may be produced from ECG systems having less than ten electrodes. In some embodiments, an ECG system comprising the four limb electrodes, and no chest electrodes, may record the six limb leads, but may not record the six chest leads. In some embodiments, an ECG system comprising the four limb electrodes, and two chest electrodes (V1 and V5) may record the six limb leads, and two of the six chest leads (V1 and V5), but may not measure the other four chest leads (V2, V3, V4, and V6). In some embodiments, an ECG system comprising the four limb electrodes, and two chest electrodes (V2 and V5) may record the six limb leads, and two of the six chest leads (V2 and V5), but may not measure the other four chest leads (V1, V3, V4, and V6).

ECG data acquired by data acquisition module 118 may be transmitted to ECG processing system 102 for storage, and processing (signal filtering, normalization, noise suppression, etc.). ECG data processing system 102 may further be configured to automatically diagnose ECG data acquired by data acquisition module 118 by executing one or more operations of one or more of the methods herein disclosed. ECG processing system 102 comprises a processor 104, and non-transitory memory 106, wherein processor 104 may read instructions from non-transitory memory 106 to execute one or more operations of one or more of the methods stored therein. ECG processing system 102 is further communicatively coupled to display device 114, and user input device 116, which may enable a user to see, and interact with, data within ECG processing system 102, respectively.

ECG processing system 102 includes a processor 104 configured to execute machine readable instructions stored in non-transitory memory 106. Processor 104 may be single core or multi-core, and the programs executed thereon may be configured for parallel or distributed processing. In some embodiments, the processor 104 may optionally include individual components that are distributed throughout two or more devices, which may be remotely located and/or configured for coordinated processing. In some embodiments, one or more aspects of the processor 104 may be virtualized and executed by remotely-accessible networked computing devices configured in a cloud computing configuration.

Non-transitory memory 106 may store deep neural network module 108, rule-based system module 110, and ECG data module 112. Deep neural network module 108 may in turn comprise deep neural network library module 180, wherein one or more trained deep neural networks may be stored, and wherein each trained deep neural network in deep neural network library module 180 may comprise a plurality of parameters (including weights, biases, and activation functions). Deep neural network module 108 may further include instructions for implementing the one or more trained deep neural networks to automatically diagnose ECG data, either alone, or in conjunction with a rule-based system stored in rule-based system module 110, by mapping the ECG data to a diagnosis, or preliminary diagnosis, using the learned parameters. For example, deep neural network module 108 and rule-based system module 110 may store instructions for implementing a hybrid ECG diagnostic system, such as hybrid ECG diagnostic system 200 shown in FIG. 2, hybrid ECG diagnostic system 300 shown in FIG. 3, and/or hybrid ECG diagnostic system 400, shown in FIG. 4. Deep neural network module 108 may include trained and/or untrained neural networks and may further include various data, or metadata pertaining to the one or more neural networks stored therein.

Deep neural network module 108 may further comprise instructions for training one or more of the deep neural networks stored therein. Deep neural network module 108 may include instructions that, when executed by processor 104, cause ECG processing system 102 to conduct one or more of the operations of method 900, and/or method 1200, discussed in more detail below. In some embodiments, deep neural network module 108 includes instructions for back-propagating error determined via a loss function to adjust one or more deep neural network parameters by implementing one or more gradient descent algorithms.

In some embodiments, deep neural network module 108 includes instructions for intelligently selecting training data pairs from ECG data module 112. In some embodiments, training data pairs comprise corresponding pairs of ECG data and ground truth diagnoses. In some embodiments, deep neural network module 108 includes instructions for selectively removing one or more lead types from ECG data of a training data pair to produce a reduced lead ECG and a corresponding ground truth diagnosis, for training a deep neural network to map features of reduced lead ECG data to diagnoses, without simulating the one or more missing lead types. In some embodiments, the deep neural network module 108 is not disposed at the ECG processing system 102.

ECG processing system 102 further includes rule-based system module 110, which may store instructions for implementing a rule-based system for diagnosing ECG data based on hard-coded cardiologist heuristics/criteria. In some embodiments, rule-based system module 110 includes instructions for extracting a plurality of pre-determined features from ECG data, and inputting the extracted features into a decision tree, wherein the decision tree comprises a plurality of branching decision points based on the extracted features. Rule-based system module 110 may work in concert with deep neural network module 108 to implement a hybrid ECG diagnostic system, such as hybrid ECG diagnostic systems 200, 300, and 400, shown in FIGS. 2, 3, and 4, respectively. In some embodiments, a preliminary diagnosis produced by a rule-based system of rule-based system module 110 may be fed to a deep neural network of deep neural network module 108, and the deep neural network may map the preliminary diagnosis to a final diagnosis. In some embodiments, the deep neural network may comprise a convolutional neural network and a decision network (comprising a multi-layer perceptron), and a preliminary diagnosis produced by the rule-based system may be input into an input layer of the decision network. The decision network may then map the preliminary diagnosis to a final diagnosis by propagating the preliminary diagnosis through a plurality of densely connected layers, until an output layer is reached. The output layer may then output a probability score associated with each of a plurality of diagnoses, and the diagnoses with the highest probability score may be displayed to a user and/or transmitted to a client device communicatively coupled to the ECG processing system 102. In some embodiments, a preliminary diagnosis produced by a deep neural network of deep neural network module 108 may be input into a rule-based system of rule-based system module 110, to be used by the rule-based system in determination of a final diagnosis.

Non-transitory memory 106 further includes ECG data module 112, which includes ECG data acquired by one or more data acquisition modules or ECG systems. In some embodiments, ECG data module 112 includes data acquired by ECG system 100. In some embodiments, ECG data module 112 may store ECG data acquired through communicative coupling with one or more data sources other than ECG processing system 102. ECG data stored within ECG data module may be organized according to one or more organizational schemes, or configured into one or more data structures known in the art of data storage. In some embodiments, ECG data may be stored in ECG data module by indexing the ECG data according to lead set, thereby enabling rapid look-up of ECG data by lead set. For example, a query for ECG data comprising the six chest leads may be executed by ECG processing system 102 by evaluating an index for each ECG data set included therein, and returning each ECG data set with an index indicating that the ECG data set includes the six chest leads.

ECG data module 112 may also store a plurality of ECG data with a corresponding plurality of ground truth diagnoses, wherein the ground truth diagnoses may be generated by expert cardiologists based on the plurality of ECG data. In some embodiments, ECG data module 112 may include a plurality of training data pairs, wherein each training data pair comprises ECG data (including either a full twelve lead ECG, or a reduced lead ECG) along with a corresponding, expert generated, ground truth diagnosis for the ECG. The training data stored within ECG data module 112 may be queried and utilized by deep neural network module 108 as part of a deep neural network training routine, such as those described in methods 900 and 1200, of FIGS. 9, and 12 below.

Turning briefly to FIG. 10, one exemplary embodiment of ECG data which may be acquired by ECG system 100 via data acquisition module 118 and electrodes 150, and stored in ECG data module 112, is shown. FIG. 10 shows electrocardiogram 1002, which comprises a twelve lead ECG, including twelve distinct waveforms/signals, which represent each of the twelve lead types. An ECG waveform for a single beat is typically referred to as a PQRST complex, as it comprises a P wave, a Q wave, an R wave, an S wave, and a T wave. An ECG waveform may further include a U wave, although this may not be present in all ECGs. The P wave appears at initiation of the beat and corresponds to activity in the atria, while the QRST complex follows the P wave and corresponds to ventricular activity. The QRS component represents the electrical activation of the ventricles, while the T wave represents the electrical recovery thereof. The ST segment is a relatively quiescent period. In humans, it has been found that the T wave is a suitable interval for detecting *alternans*. That is, a level of variations in the T waves of alternating beats is a good indicator of a patient's cardiac electrical stability. In some embodiments, the features of an ECG waveform which may be analyzed to diagnose an ECG comprise the amplitudes for each of the P, Q, R, S, T and U waves, as well as the time between one or more of the P, Q, R, S, T, and U waves, which are referred to as intervals or segments. For example, the interval of time between initiation of the P wave and initiation of the QRS complex is referred to as the PR interval, and may be used to diagnose the physiological condition of a heart. In another example, the duration of time between initiation of the Q wave and termination of the T wave, referred to as the QT interval, may be used to diagnose the physiological condition of the heart. Further diagnostic features of an ECG include a heart rate, which may be determined from the beat to beat interval (such as a Q-Q interval, a T-T interval, etc.) and the beat to beat variation in P, Q, R, S, and T amplitudes and/or intervals.

In some embodiments, the non-transitory memory 106 may include components disposed at two or more devices, which may be remotely located and/or configured for coordinated processing. In some embodiments, one or more aspects of the non-transitory memory 106 may include remotely-accessible networked storage devices configured in a cloud computing configuration.

ECG system 100 further includes user input device 116. User input device 116 may comprise one or more of a touchscreen, a keyboard, a mouse, a trackpad, a motion sensing camera, or other device configured to enable a user to interact with and manipulate data within ECG processing system 102. As an example, user input device 116 may enable a user to make a selection of ECG data to diagnose.

Display device 114 may include one or more display devices utilizing virtually any type of technology. In some embodiments, display device 114 may comprise a computer monitor, and may display unprocessed and processed ECGs data. Display device 114 may be combined with processor 104, non-transitory memory 106, and/or user input device 116 in a shared enclosure, or may be peripheral display devices and may comprise a monitor, touchscreen, projector, or other display device known in the art, which may enable a user to view ECG data and/or interact with various data stored in non-transitory memory 106.

It should be understood that ECG system 100 shown in FIG. 1 is for illustration, not for limitation. Another appropriate ECG processing system may include more, fewer, or different components.

Figure 2:
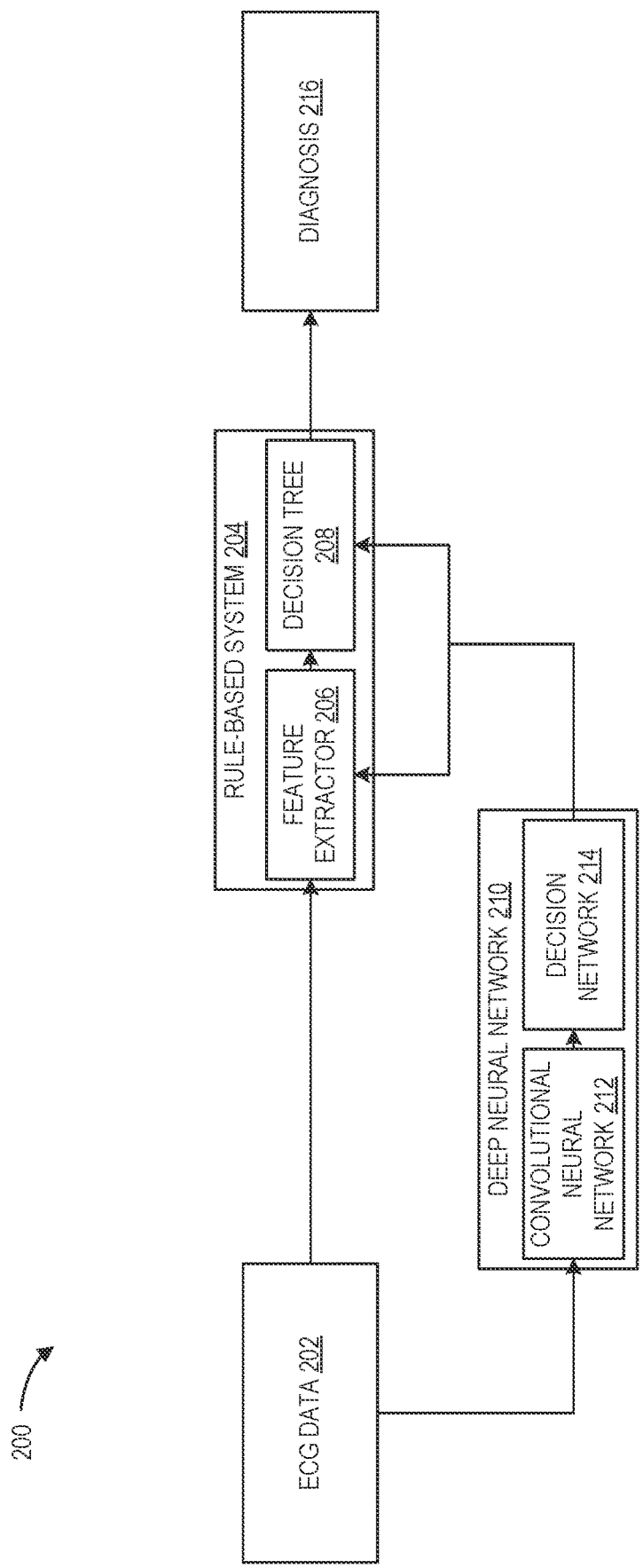
FIG. 2 is a schematic diagram illustrating a first embodiment of a hybrid ECG diagnostic system.

Turning to FIG. 2, a first embodiment of a hybrid ECG diagnostic system 200 is shown. In some embodiments, hybrid ECG diagnostic system 200 may be implemented by the ECG processing system 102, an edge device connected to the ECG processing system 102, a cloud device in communication with the ECG processing system 102, or any appropriate combination thereof.

Hybrid ECG diagnostic system 200 comprises a deep neural network 210, and a rule-based system 204, configured to receive ECG data 202, and to produce diagnosis 216 based on the received ECG data. In some embodiments, hybrid ECG diagnostic system may be configured to further receive auxiliary inputs (not shown). In some embodiments, ECG data 202 may comprise a live stream of ECG data acquired from an ECG system, such as ECG system 100. In some embodiments, ECG data 202 may comprise pre-recorded ECG data, which may be transmitted to hybrid ECG diagnostic system 200 from a communicatively coupled data storage device, such as from ECG data module 112 in non-transitory memory 106. In some embodiments, ECG data 202 may comprise a twelve lead ECG. In some embodiments, ECG data 202 may comprise fifteen lead data. In some embodiments, ECG data 202 may be a reduced lead set ECG comprising less than twelve leads, but more than zero leads.

In hybrid ECG diagnostic system 200, ECG data 202 is first input into deep neural network 210. In some embodiments, deep neural network 210 comprises two deep neural networks connected in series, the first is convolutional neural network 212, comprising a plurality of convolutional layers, and the second is decision network 214, comprising a plurality of densely connected layers (and therefore decision network 214 may also be referred to as a multi-layer perceptron, or MLP). Output from an output layer of convolutional neural network 212 is received at an input layer of decision network 214, and mapped to a plurality of probability scores for each of a plurality of pre-determined diagnoses. In some embodiments, deep neural network 210 may have been intelligently selected from a deep neural network library, such as deep neural network library 1104 shown in FIG. 11, based on a lead set used to train the deep neural network 210 matching a lead set in ECG data 202. In some embodiments, deep neural network 210 may have been selected according to one or more operations of method 1300 shown in FIG. 13.

Convolutional neural network 212 is configured to receive ECG data 202 at an input layer. In some embodiments, one or more pre-processing operations may be conducted on ECG data 202 prior to being input into convolutional neural network 212. In some embodiments, pre-processing may include one or more of ECG normalization (wherein the range of ECG data is mapped to a range from 0 to 1), noise reduction, binarization of intensity values, ECG waveform thinning, etc. In some embodiments, convolutional neural network 212 is configured to receive ECG data 202 as a 2D data object, comprising a first dimension of electric potential, and a second dimension of time. In embodiments where ECG data 202 comprises a 2D data objet, the input layer of convolutional neural network 212 may be configured as a 2D grid of input nodes/neurons, wherein each input node/neuron may receive as input a distinct value of the 2D ECG data. In some embodiments, ECG data 202 may comprise one or more 2D images, wherein the ECG waveform data is displayed graphically within the 2D images, such that the ECG waveform data is encoded by a plurality of pixel intensity values of a 2D image. In such embodiments, the input layer of convolutional neural network 212 may comprise an equal number of input nodes/neurons as there are pixels in the one or more 2D images, thereby enabling a 1-to-1 input of pixel intensity values into input nodes/neurons of an input layer of convolutional neural network 212.

After ECG data 202 is input into convolutional neural network 212, the data is propagated through one or more convolutional layers, wherein, in each convolutional layer, one or more filters is applied to the input ECG data 202, to produce a feature map. Each filter comprises one or more weights, the weights mapping a subregion of an input space to a subregion of a feature map. In general, filters may be applied to detect local conjunctions of features in input data (feature maps and/or ECG data 202). In some embodiments, filters may comprise a 3-by-3 grid of weights, wherein data from a 3-by-3 grid of input values (e.g., ECG data 202 or features from a previous feature map) is mapped to a single output value by computing a dot product between the 3-by-3 grid of input values and the 3-by-3 grid of weights. In some embodiments, each of the one or more weights of a filter may be learned during a training phase. The depth of the feature map corresponds to the number of filters applied, whereas the height and width of the feature map corresponds to the height and width of the input ECG data 202 (or the previous feature map from which the current convolutional layer is receiving data). The feature map quantifies the degree of match between the one or more applied filters and each spatial region within the input data.

Data from a feature map may be passed through a non-linearity layer and/or a rectification layer, to produce an activation map, and the activation map may be taken as input by a subsequent layer. In some embodiments, a combined rectification and non-linearity layer may be used, such as a rectified linear unit (ReLU). Convolutional neural network 212 may further include additional convolutional layers (wherein feature maps or activation maps from previous convolutional layers may be taken as input and filtered/convolved again, to produce feature maps/activation maps comprising higher order features/composite features), pooling layers (wherein each subregion of ECG data 202 or a feature map is down sampled to produce a lower spatial resolution feature map), dropout layers (wherein one or more weights or filters are dropped during a training phase to reduce a probability of overfitting), and regularization layers, and fully connected/densely connected layers (wherein each output/activation/feature of a previous feature map or activation map is received by each node/neuron of a subsequent layer).

The one or more filters of each convolutional layer of convolutional neural network 212 may be learned during a training process, and thereby may not require hard-coding by a domain expert, such as a cardiologist, thus enabling convolutional neural network 212 to learn to identify and extract features correlated with accurate diagnostic predictions, instead of utilizing pre-determined features. A technical effect of utilizing a hybrid ECG diagnostic system, such as hybrid ECG diagnostic system 200, to diagnose ECG data, is that a deep neural network within the hybrid ECG diagnostic system may learn to identify use-case specific features correlated with diagnostic predictions automatically, by training on use-case specific data, without requiring manual updating of hard-coded rules.

Convolutional neural network 212 further includes an output layer, wherein the output layer is configured to output a plurality of features extracted/identified in ECG data 202. In some embodiments, output from convolutional neural network 212 comprises a feature map, indicating a probability of occurrence for each of a plurality of learned features, at each of a plurality of sub regions within ECG data 202. It will be appreciated, that although the terminology used to describe feature extractor 206, and convolutional neural network 212, is similar, as both feature extractor 206 and convolutional neural network 212 determine/extract features within ECG data, it will be appreciated that convolutional neural network 212 detects learned features at each sub region of ECG data 202, whereas feature extractor 206 is extracts pre-selected/pre-determined features, as discussed in more detail herein. Further, convolutional neural network 212 and feature extractor 206 are configured to extract/determine features substantially different manners.

Output from convolutional neural network 212 may be fed to decision network 214. In some embodiments, output from convolutional neural network 212 comprises a plurality of features identified in ECG data 202. Decision network 214 comprises an input layer having a plurality of input nodes/neurons, wherein the number of input nodes/neurons may, in some embodiments, be equal to the number of features output by convolutional neural network 212. In some embodiments, the number of input nodes/neurons in an input layer of decision network 214 may be greater than a number of output features from convolutional neural network 212, thereby enabling decision network 214 to receive additional data from one or more sources.

Decision network 214 comprises an input layer, an output layer, and one or more hidden layers, wherein each hidden layer comprises a densely/fully connected layer. The architecture of decision network 214 may also be referred to as a multi-layer perceptron (MLP). Each neuron of each hidden layer produces an output by computing a dot product between each output of each node in a preceding layer using a plurality of weights, wherein each weight is uniquely correlated with a neuron of the preceding layer. Mathematically this can be expressed by the below equation.

$$Y_j = f\left(\sum_{i=1}^{n} W_{ji} X_i + B_j\right)$$

Where $X_i$ is the i-th neuron of the preceding layer, $Y_j$ is the output/activation of the j-th neuron of the current layer, $W_{ji}$ is the weight/strength of the connection between the i-th neuron of the preceding layer and the j-th neuron of the current layer, and $B_j$ is the bias of the j-th neuron in the current layer. In some embodiments, the activation function $f$ is a rectified linear unit (ReLU) function, for example. In some embodiments, $f$ may comprise a plain ReLU function, a leaky ReLU function, a parametric ReLU function, etc. In some embodiments $f$ may comprise a hyperbolic tangent function, a softplus function, a soft exponential function, a sigmoid function, and other activation functions known in the art of machine learning. Decision network may comprise substantially any number of hidden layers.

The output layer of decision network 214 comprises a plurality of output neurons. In some embodiments, each output neuron may correspond to a different diagnosis, and a value output from a neuron of an output layer may represent/indicate a probability score for the diagnosis associated with the neuron. For example, neuron J in an output layer, which corresponds to diagnosis K, may output a probability score between 0 and 1, wherein the probability score indicates a predicted probability of diagnosis K applying to the input ECG data 202, specifically, if neuron J outputs a probability score of approximately 0, this indicates a relatively low probability of diagnosis K applying to ECG data 202, whereas if neuron J outputs a probability score of approximately 1, this indicates a relatively high probability of diagnosis K applying to ECG data 202. Output from the output layer of decision network 214 may comprise a vector of probability scores, one probability score for each of a pre-determined plurality of diagnoses. The vector of probability scores produced by the output layer of decision network 214 may be referred to as a preliminary diagnosis, as the probability scores may be fed into rule-based system 204 for further analysis/diagnosis. Specifically, the preliminary diagnosis produced by deep neural network 210 is fed to feature extractor 206 and decision tree 208 of rule-based system 204.

Rule-based system 204 comprises feature extractor 206, and decision tree 208, and may be configured to receive ECG data 202 at feature extractor 206, as well as to receive a preliminary diagnosis at one or both of feature extractor 206 and decision tree 208.

In some embodiments, feature extractor 206 may perform one or more pre-processing operations on ECG data 202. In some embodiments, feature extractor 206 may determine a region of interest in received 2D ECG data, and invert the color data in the region of interest to produce a black ECG signal/waveform on a white background. Feature extractor 206 may then binarize the 2D ECG data (that is, each pixel of the 2D ECG data below an intensity threshold may be set to black, and each pixel of the 2D ECG data above an intensity threshold may be set to white, producing a 2D ECG image comprising pixels with a binary intensity distribution, wherein each pixel of the ECG data 202 is either white or black, 1 or 0). Following binarization of the ECG waveform, one or more operations of noise rejection may be performed, to remove isolated black pixels (that is, black pixels not connected to the ECG waveform). Feature extractor 206 may also thin the ECG waveform by setting the thickness of the ECG waveform to one pixel, thereby reducing redundant information contained in the ECG waveform. Thus, feature extractor 206 may pre-process ECG data 202, to enable more efficient feature extraction and diagnosis. Further, after pre-processing, information contained in ECG data 202 may be more easily stored/processed, as redundant data may be reduced or eliminated.

Feature extractor 206 comprises hard-coded machine executable instructions for determining one or more pre-determined features of ECG data 202. In some embodiments, pre-determined features of an ECG include the amplitude, area, and duration/time interval of each wave (P, Q, R, S, T, and U), as well as intervals/durations between waves (of either the same type, or if different types). In some embodiments, feature extractor 206 is configured to determine one or more amplitudes and/or intervals of a waveform within an ECG. In some embodiments, feature extractor 206 may determine an amplitude and period for one or more of a P wave, a Q wave, an R wave, an S wave, a T wave, a U wave, or a complex formed by a combination of two or more of the above waves. In some embodiments feature extractor 206 may be configured to determine one or more periods/intervals within an ECG waveform such as an inter-wave interval/duration, or a duration of a single wave. The feature extractor may determine a heart rate by determining an interval/duration between corresponding features of a same wave type, for example, by measuring a duration of time between crests of a first Q wave and a second Q wave, a heart rate may be determined. The feature extractor may average one or more intervals/durations to determine a heart rate or may extrapolate a heart rate based on a single measured interval. Further, the feature extractor may determine one or more beat-to-beat variations in one or more of the above discussed waves. Feature extractor 206 comprises hard-coded, pre-determined ECG features, wherein the pre-determined ECG features may be determined by expert cardiologists, and may comprise humanly intuitive waveform features.

Following pre-processing, feature extractor 206 may fit a baseline (also referred to as the isoelectric line) to ECG waveform data. In some embodiments, feature extractor 206 may determine a baseline by fitting a straight horizontal line through the largest number of black pixels in the ECG waveform (wherein a horizontal line, as used herein, will be understood to refer to a line running substantially parallel to an X-axis, of an ECG, wherein the X-axis is conventionally a time domain of the ECG) and setting this straight horizontal line as the baseline. The baseline enables feature extractor 206 to determine an amplitude and interval of each wave comprising the ECG. In some embodiments, an amplitude of a wave may be determined as the difference in the Y-dimension (electrical potential) between the peak of a wave and the baseline, whereas the interval/duration of a wave may comprise the difference in the X-dimension (time) between initial departure of a wave from the baseline, and the point on the X-axis at which the wave returns to the baseline. In some embodiments, feature extractor 206 may fit each wave of ECG data 202 with a rectangle, wherein each rectangle's base runs parallel with, and at a same height (Y-dimension) as, the baseline. The height (Y-dimension) of each rectangle corresponds to the height/amplitude (Y-dimension) of each corresponding wave, and the width (X-dimension) of each wave corresponds to the duration/interval of each wave. Further, feature extractor 206 may approximately determine an area of each wave based on the area (height multiplied by width) of each corresponding rectangle. In some embodiments, feature extractor 206 may uniquely identify each wave of an ECG waveform by first determining which wave comprises the largest amplitude, and labeling this wave as the R wave. Feature extractor 206 may then determine the identity of the other waves (P, Q, S, T, and U) based on their location along the X-axis relative to the R wave. For example, feature extractor 206 may label a wave immediately preceding the R wave as the Q wave, and may in turn label a wave immediately preceding the Q wave as the P wave). Similarly, feature extractor 206 may label a wave immediately following the R wave as the S wave, and may label a wave immediately following the S wave as the T wave etc.

The features determined by feature extractor 206 may be fed to decision tree 208. In some embodiments, decision tree 208 comprises one or more root nodes, one or more decision nodes or sub nodes, and one or more leaf nodes. Features extracted by feature extractor 206 may be input into one or more root nodes, wherein the features may be evaluated based on one or more pre-determined, expert criteria/heuristics. Each node, other than the leaf nodes, may comprise one or more sub-nodes. The evaluation at each node may determine to which sub node the features are propagated to. The sub nodes branching from a given node may in turn comprise one or more sub nodes, and this pattern may continue until one or more leaf nodes is reached. Each node which branches to two or more sub nodes may be referred to as a decision node, as a "decision" between which sub-node is to be selected is made therein. At each decision node, the features of ECG data 202 determined by feature extractor 206 may be evaluated based on expert criteria, and the result of the evaluation may determine to which sub node the extracted features are propagated. A terminal node, also referred to as a leaf node, may comprise one or more diagnoses. Decision tree 208 may comprise a plurality of leaf nodes, each uniquely corresponding to a distinct diagnosis. The extracted features of ECG data 202 propagate through the branching structure of decision tree 208, until one or more leaf nodes are reached, and a diagnosis, such as diagnosis 216, is determined based on the one or more leaf nodes.

In hybrid ECG diagnostic system 200, a preliminary diagnosis produced by deep neural network 210 may be fed to one or both of feature extractor 206 and decision tree 208. The preliminary diagnosis produced by deep neural network 210 may be used to modify one or more features determined by feature extractor 206 and/or to modify a final diagnosis 216 produced by decision tree 208. In some embodiments, a preliminary diagnosis produced by deep neural network 210 may be used by rule-based system 204 to assess and/or modify a confidence of a diagnosis 216. For example, if the diagnosis 216 produced by rule-based system 204 is the same as a preliminary diagnosis produced by deep neural network 210, rule-based system 204 may indicate a high confidence rating for the diagnosis. Conversely, if the diagnosis 216 produced by rule-based system 204 deviates from the preliminary diagnosis produced by deep neural network 210, rule-based system 204 may indicate a low confidence rating for the diagnosis. In some embodiments, diagnosis 216 may include a confidence rating, indicating a degree of agreement/disagreement between a preliminary diagnosis produce by deep neural network 210, and rule-based system 204.

Diagnosis 216 may be displayed to a user via a display device, such as device 114. In some embodiments, diagnosis 216 may be transmitted to one or more client devices, edge computing devices, servers, cloud storage devices, etc.

Figure 3:
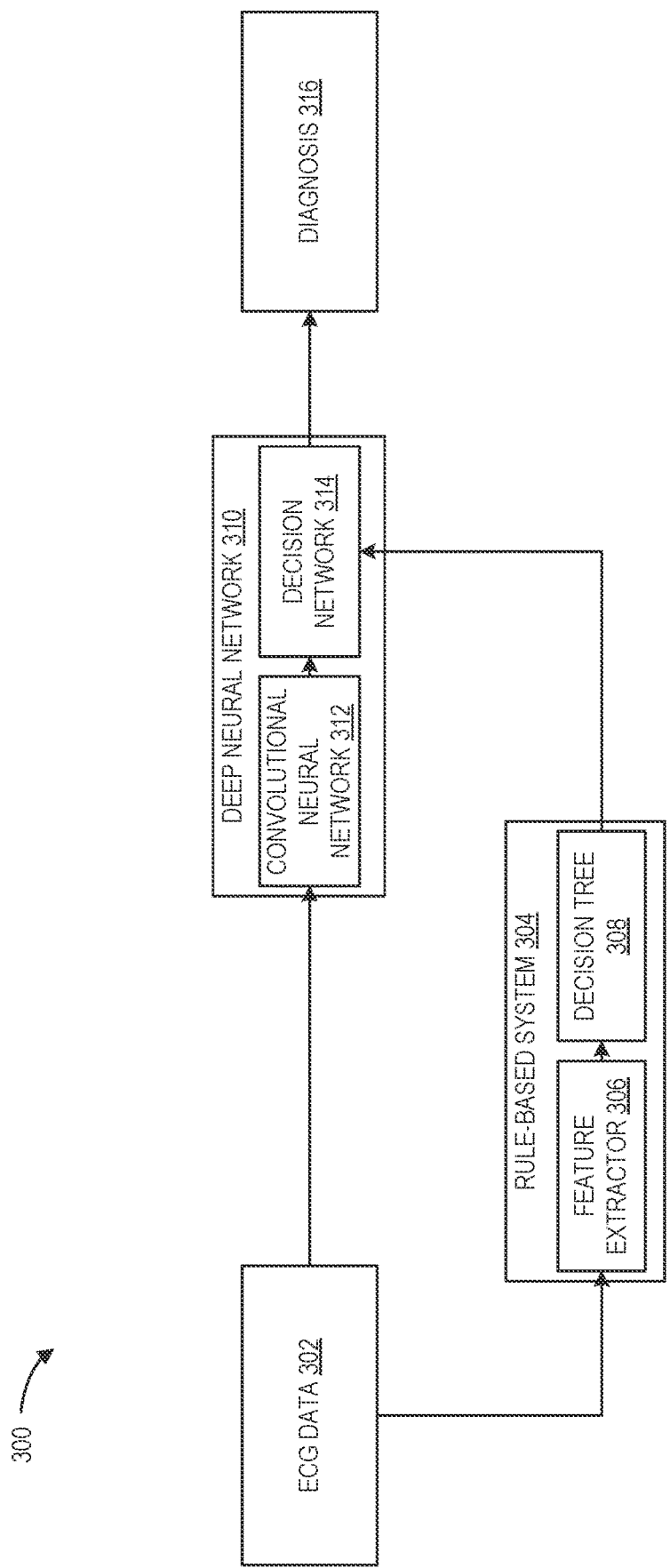
FIG. 3 is a schematic diagram illustrating a second embodiment of hybrid ECG diagnostic system.

Turning to FIG. 3, a second embodiment of a hybrid ECG diagnostic system 300 is shown. In some embodiments, hybrid ECG diagnostic system 300 may be implemented by the ECG processing system 102, an edge device connected to the ECG processing system 102, a cloud device in communication with the ECG processing system 102, or any appropriate combination thereof. In hybrid ECG diagnostic system 300, rule-based system 304 determines a preliminary diagnosis from ECG data 302 based on hard-coded expert criteria, which is fed into an input layer of decision network 314 of deep neural network 310, along with a plurality of features determined by convolutional neural network 312 from ECG data 302. Decision network 310 then maps both the plurality of features produced by convolutional neural network 312 and the preliminary diagnosis produced by rule-based system 304 to diagnosis 316. In this way, deep neural network 310 is informed of a preliminary diagnosis produced using hard-coded expert criteria, which may be used by decision network 314 to produce a more accurate diagnosis 316 for ECG data 302. Said another way, a preliminary diagnosis produced by rule-based system 304 may be updated/modified by decision network 314, based on learned features extracted from ECG data 302, thereby adding additional flexibility and accuracy on top of diagnoses produced by rule-based system 304.

In some embodiments, ECG data 302 may comprise a live stream of ECG data acquired from an ECG system, such as ECG system 100. In some embodiments, ECG data 302 may comprise pre-recorded ECG data, which may be transmitted to hybrid ECG diagnostic system 300 from a communicatively coupled data storage device, such as from ECG data module 112 in non-transitory memory 106. In some embodiments, ECG data 302 may be a twelve lead ECG. In some embodiments, ECG data 302 may be a fifteen lead ECG. In some embodiments, ECG data 302 may be a reduced lead set ECG comprising less than twelve leads, but more than zero leads. ECG data 302 may be transmitted to both rule-based system 304 and deep neural network 310, in either a sequential or parallel manner.

Rule-based system 304 comprises feature extractor 306, and decision tree 308, which may be configured to receive ECG data 302 at feature extractor 306, and produce/determine a preliminary diagnosis based thereon. Rule-based system 304 may be configured in a manner substantially analogous to that of rule-based system 204, which is described above, however, rule-based system 304 may, in some embodiments, not be configured to receive a preliminary diagnosis from deep neural network 310. Feature extractor 306 may perform one or more pre-processing operations on ECG data 302 in a manner analogous to that described above with reference to feature extractor 206.

Following pre-processing, feature extractor 306 may determine one or more pre-determined features of ECG data 302, such as is described in more detail above, with reference to feature extractor 206. The features determined by feature extractor 206 may be fed to decision tree 308, which is configured in a manner substantially similar to decision tree 208, described above. Briefly, the extracted features of ECG data 302 propagate through the branching structure of decision tree 308, until one or more leaf nodes are reached, and a preliminary diagnosis is determined based on the one or more leaf nodes. The preliminary diagnosis produced by decision tree 308 may be transmitted to an input layer of decision network 314 of deep neural network 310.

Deep neural network 310 may be configured in a manner substantially analogous to deep neural network 210. Deep neural network 310 comprises two deep neural networks connected in series, the first is convolutional neural network 312, comprising a plurality of convolutional layers, and the second is decision network 314, comprising a plurality of densely connected layers (and therefore decision network 314 may also be referred to as a multi-layer perceptron, or MLP).

Convolutional neural network 312 may comprise a convolutional neural network analogous to convolutional neural network 212, which is described above. Convolutional neural network 312 comprises one or more convolutional layers including one or more learned filers, and is configured to receive ECG data 302 at an input layer, and map ECG data 302 to a plurality of features/feature map using the one or more learned filters. In some embodiments, output produced by convolutional neural network 312 may comprise a feature map, which may be input into an input layer of decision network 314, along with the preliminary diagnosis produced by decision tree 308.

Decision network 314 may be configured in a manner substantially analogous to decision network 214, however, decision network 314 is configured to receive both output from convolutional neural network 312, and a preliminary diagnosis produced by decision tree 308. In some embodiments, the input layer of decision network 314 may comprise a first plurality of neurons configured to receive the plurality of features/feature map output by an output layer of convolutional neural network 312, and a second plurality of neurons configured to receive the preliminary diagnosis produced by decision tree 308. A technical effect of inputting a preliminary diagnosis into an input layer of decision network 314 is that deep neural network 310 may adjust/modify the preliminary diagnosis based on one or more features identified by convolutional neural network 312 in ECG data 302, wherein the convolutional neural network 312 may learn to extract/identify ECG features correlated with correct diagnoses in use-case specific data, without reprogramming/re-coding. Output from an output layer of convolutional neural network 312 is received at an input layer of decision network 314, along with the preliminary diagnosis produced by decision tree 308 of rule-based system 310, and mapped to diagnosis 316. In some embodiments, diagnosis 316 comprises a plurality of probability scores for each of a plurality of pre-determined diagnoses. In some embodiments, diagnosis 316 comprises a vector of probability scores, wherein each row of the vector corresponds to a distinct diagnosis or diagnostic feature.

In some embodiments, deep neural network 310 may be intelligently selected from a deep neural network library, such as deep neural network library 1104 shown in FIG. 11, based on a lead set used to train the deep neural network 310 matching a lead set in ECG data 302. In some embodiments, deep neural network 310 may have been selected according to one or more operations of method 1300 shown in FIG. 13.

Figure 4:
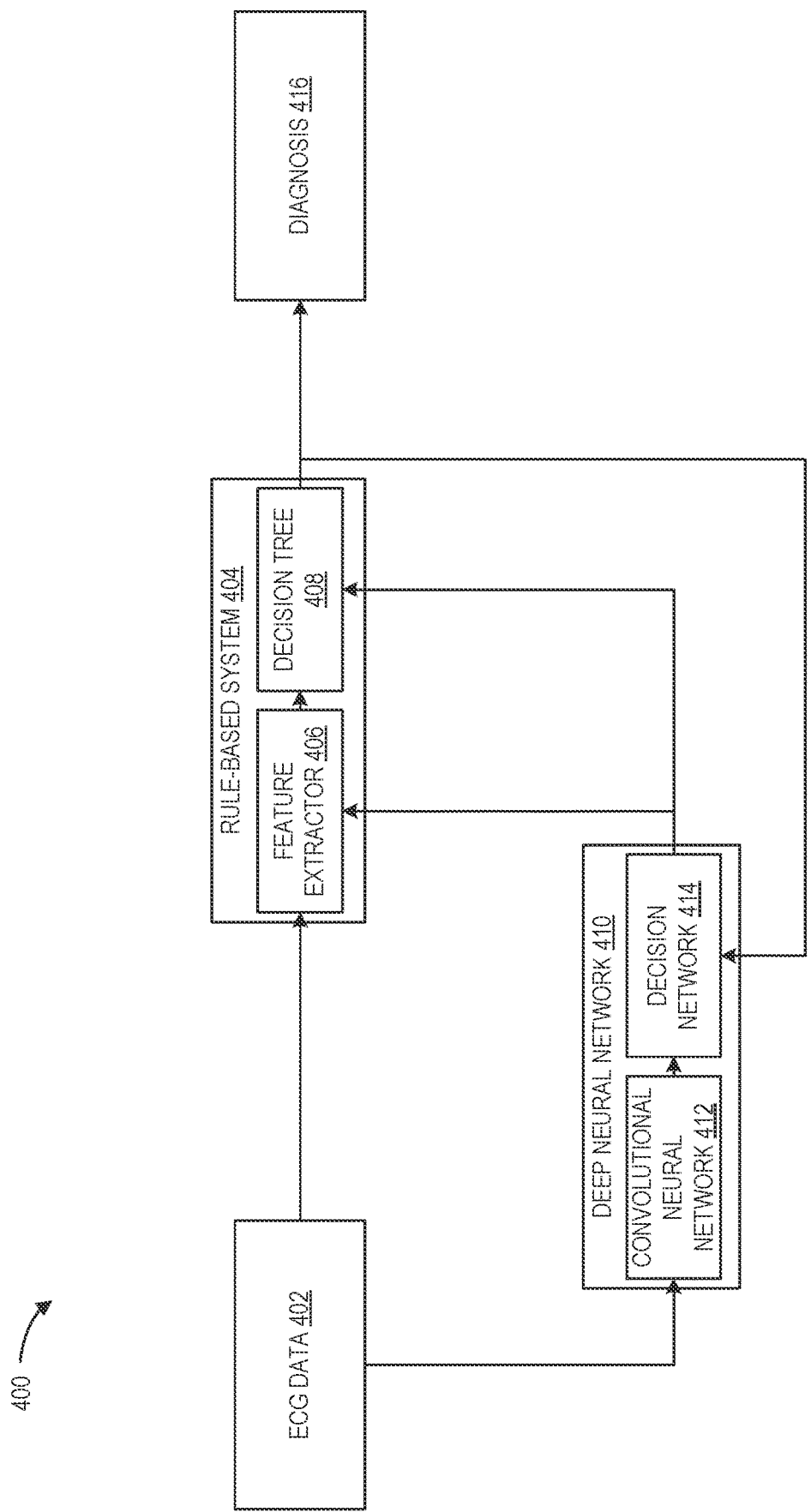
FIG. 4 is a schematic diagram illustrating a third embodiment of a hybrid ECG diagnostic system.

Turning to FIG. 4, a third embodiment of a hybrid ECG diagnostic system 400 is shown. In some embodiments, hybrid ECG diagnostic system 400 may be implemented by the ECG processing system 102, an edge device connected to the ECG processing system 102, a cloud device in communication with the ECG processing system 102, or any appropriate combination thereof. In hybrid ECG diagnostic system 400, ECG data 402 is fed to rule-based system 404, which produces a first preliminary diagnosis based on ECG data 402. The first preliminary diagnosis is then transmitted to deep neural network 410, which maps both the first preliminary diagnosis and ECG data 402 to a second preliminary diagnosis. The second preliminary diagnosis is then fed back into rule-based system 404, and used to produce diagnosis 416. In this way, hybrid ECG diagnostic system 400 may incorporate adaptive feature mapping of a deep neural network, with an intuitive and transparent decision making model reflecting expert criteria, to produce a diagnosis tailored to a specific use-case, and with a greater transparency than may be achieved in deep neural networks alone.

In some embodiments, ECG data 402 may comprise a live stream of ECG data acquired from an ECG system, such as ECG system 100. In some embodiments, ECG data 402 may comprise pre-recorded ECG data, which may be transmitted to hybrid ECG diagnostic system 400 from a communicatively coupled data storage device, such as from ECG data module 112 in non-transitory memory 106. In some embodiments, ECG data 402 may be a twelve lead ECG. In some embodiments, ECG data 402 may be a fifteen lead ECG. In some embodiments, ECG data 402 may be a reduced lead set ECG comprising less than twelve leads, but more than zero leads. ECG data 402 may be transmitted to both rule-based system 404 and deep neural network 410, in either a sequential or parallel manner.

Rule-based system 404 comprises feature extractor 406, and decision tree 408, which may be configured to receive ECG data 402 at feature extractor 406, and produce/determine a first preliminary diagnosis based thereon. Rule-based system 404 is further configured to incorporate a second preliminary diagnosis produced by deep neural network 410 into one or more of feature extractor 406 and decision tree 408, and to determine diagnosis 416 based on ECG data 402 in conjunction with the second preliminary diagnosis. Feature extractor 406 may perform one or more pre-processing operations on ECG data 402 in a manner analogous to that described above with reference to feature extractor 406. Following pre-processing, feature extractor 406 may determine one or more pre-determined features of ECG data 402, such as is described in more detail above, with reference to feature extractor 206. In some embodiments the second preliminary diagnosis produced by deep neural network 410 may be used to update/modify one or more parameters of feature extractor 406.

The features determined by feature extractor 406 may be fed to decision tree 408, which is configured in a manner substantially similar to decision tree 208, described above. In some embodiments the second preliminary diagnosis produced by deep neural network 410 may be used to update/modify one or more parameters of decision tree 408. Briefly, the extracted features of ECG data 402 may propagate through the branching structure of decision tree 408, until one or more leaf nodes are reached, and the first preliminary diagnosis is determined based on the one or more leaf nodes. The first preliminary diagnosis produced by decision tree 408 may be transmitted to an input layer of decision network 414 of deep neural network 410.

Deep neural network 410 may be configured in a manner substantially analogous to deep neural network 210. Deep neural network 410 comprises two deep neural networks connected in series, the first is convolutional neural network 412, comprising a plurality of convolutional layers, and the second is decision network 414, comprising a plurality of densely connected layers (and therefore decision network 414 may also be referred to as a multi-layer perceptron, or MLP).

Convolutional neural network 412 may comprise a convolutional neural network analogous to convolutional neural network 212, which is described above. Convolutional neural network 412 comprises one or more convolutional layers including one or more learned filers, and is configured to receive ECG data 402 at an input layer, and map ECG data 402 to a feature map/plurality of features using the one or more learned filters. In some embodiments, output produced by convolutional neural network 412 may comprise a feature map, which may be input into an input layer of decision network 414, along with the first preliminary diagnosis produced by decision tree 408.

Decision network 414 may be configured in a manner substantially analogous to decision network 214, however, decision network 414 is configured to receive both output from convolutional neural network 412, and the first preliminary diagnosis produced by decision tree 408. In some embodiments, the input layer of decision network 414 may comprise a first plurality of neurons configured to receive the plurality of features/feature map output by an output layer of convolutional neural network 412, and a second plurality of neurons configured to receive the first preliminary diagnosis produced by decision tree 408. A technical effect of inputting the first preliminary diagnosis into an input layer of decision network 414, along with the plurality of features mapped from ECG data 402 by convolutional neural network 412, is that deep neural network 410 may adjust/modify the first preliminary diagnosis based the on one or more features identified by convolutional neural network 412 in ECG data 402, wherein the convolutional neural network 412 may learn to extract/identify ECG features correlated with ground truth diagnoses in use-case specific data, without reprogramming/re-coding.

Output from an output layer of convolutional neural network 412 is received at an input layer of decision network 414, along with the first preliminary diagnosis produced by decision tree 408 of rule-based system 410, and mapped to a second preliminary diagnosis. In some embodiments, the second preliminary diagnosis comprises a plurality of probability scores for each of a plurality of pre-determined diagnoses. In some embodiments, the second preliminary diagnosis comprises a vector of probability scores, wherein each row of the vector corresponds to a distinct diagnosis or diagnostic feature.

In some embodiments, deep neural network 410 may be intelligently selected from a deep neural network library, such as deep neural network library 1104 shown in FIG. 11, based on a lead set used to train the deep neural network 410 matching a lead set in ECG data 402 (that is, the lead types present in data used to train the deep neural network 410 are the same as the lead types present in ECG data 402). In some embodiments, deep neural network 410 may have been selected according to one or more operations of method 1300 shown in FIG. 13.

The second preliminary diagnosis produced by decision network 414 of deep neural network 410 may be fed back to rule-based system 404, and one or more parameters of feature extractor 406 and/or decision tree 408 may be adjusted based thereon. In some embodiments, the second preliminary diagnosis may be used by rule-based system 404 to determine a confidence/certainty of a final diagnosis 416. Following receipt of the second preliminary diagnosis produced by deep neural network 410, rule-based system 404 may re-evaluate ECG data 402 to produce diagnosis 416. Diagnosis 416 may comprise a final diagnosis, and may be stored in memory, displayed via a display device, and/or transmitted to one or more client devices. In this way, hybrid ECG diagnostic system 400 incorporates a recursive/feedback diagnostic scheme, wherein an initial diagnostic prediction of rule-based system 404 may be used to form a diagnostic prediction of deep neural network 410, which is in turn used by rule-based system 404 to produce a final diagnostic prediction. A technical effect of the above described recursive diagnostic scheme is that diagnostic accuracy, confidence, and consistency may be enhanced.

Figure 5:
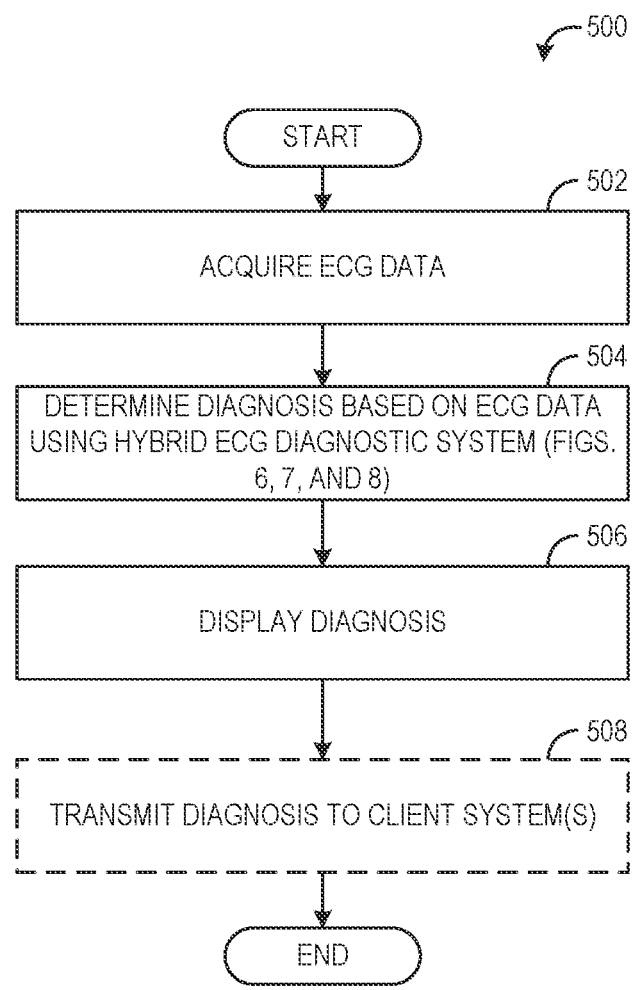
FIG. 5 is a high level flow chart illustrating a method for automatically diagnosing acquired ECG data using a hybrid system.

Turning to FIG. 5, a flow chart of an exemplary method 500 for diagnosing ECG data using a hybrid ECG diagnostic system is shown. In some embodiments, method 500 may be executed by ECG system 100, an edge device connected to ECG system 100, a cloud device in communication with ECG system 100, or any appropriate combination thereof. Method 500 may enable automatic, accurate, and use-case specific diagnosis of one or more ECGs for one or more patients.

Method 500 begins at 502, where ECG data is acquired by an ECG system. ECG data may comprise one or more lead signals/waveforms, indicating an electrical activity of a heart through time. In some embodiments, acquiring ECG data may comprise measuring a twelve lead ECG using ten electrodes in electrical contact with a patient, as described in more detail above, with reference to FIG. 1. In some embodiments, acquiring ECG data may comprise measuring a fifteen lead ECG using thirteen electrodes. In some embodiments, acquiring ECG data may comprise measuring a reduced lead ECG using less than ten electrodes. Acquired ECG data may be stored in memory for later processing. In some embodiments, the ECG data acquired at operation 502 comprises 2D data of electrical potential through time, wherein electrical potential is plotted along the y-axis, and time is plotted along the x-axis. ECG data acquired at operation 502 may be stored in one or more formats, including SCP-ECG, DICOM-ECG, HL7 aECG, and other storage formats known in the art of ECGs. Acquisition of ECG data at operation 502 may occur under various conditions, such as when the patient is resting, during exercise, or in an ambulance.

At operation 504, a diagnosis is determined for the ECG data acquired at operation 502 using one or more of hybrid ECG diagnostic systems 200, 300, and/or 400, by executing one or more of methods 600, 700, and/or 800. In a first exemplary embodiment, operation 504 comprises hybrid ECG diagnostic system 200 executing one or more operations of method 600, to determine a diagnosis based on acquired ECG data. In a second exemplary embodiment, operation 504 comprises hybrid ECG diagnostic system 300 executing one or more operations of method 700, to determine a diagnosis based on acquired ECG data. In a third embodiment, operation 504 comprises hybrid ECG diagnostic system 400 executing one or more operations of method 800, to determine a diagnosis based on acquired ECG data. In some embodiments, the ECG system executing method 500 may select between the first, second, and third embodiments of a hybrid ECG diagnostic system based on one or more features of the acquired ECG data.

At operation 506, the diagnosis is displayed via a display device. The diagnosis may indicate if the ECG data includes an abnormality (arrhythmia), as well as an indication of which features of the ECG manifest/display the abnormality. In the case of a normal/healthy ECG, the diagnosis may indicate that no arrhythmia/abnormality was detected. In some embodiments, the display device comprises a graphical user interface wherein the diagnosis may be displayed to a user. In some embodiments, the display device may comprise a device coupled to the ECG system, such as display device 114, which may be viewed by an operator of ECG system. The operator may view the displayed diagnosis, and may take one or more actions based thereon. The diagnosis may include one or more lines of text indicating one or more features of the ECG data, along with a diagnostic assessment of the one or more features. Turning briefly to FIG. 10, two exemplary embodiments of diagnoses are shown, first diagnosis 1004, produced using a rule-based system without a deep neural network, and second diagnosis 1006, produced using a hybrid ECG diagnostic system, such as hybrid ECG diagnostic system 200, 300, and 400, discussed herein. As seen in FIG. 10, first diagnosis 1004 includes a textual message indicating an assessment of the rhythm, contour including the QRS complex, ST-T wave, and the overall normality/abnormality of ECG 1002, as well as one or more physiological mechanisms underlying the indicated normality/abnormality. Likewise, second diagnosis 1006 includes a message, indicating a diagnostic assessment of the rhythm, contour including QRS complex, ST-T wave, and one or more physiological features of the heart, and the overall normality/abnormality of ECG 1002, as well as one or more physiological mechanisms underlying the indicated normality/abnormality, like electrolyte imbalance, possible location of blocked coronary artery, etc.

At operation 508, the ECG system may transmit the diagnosis to one or more client systems. Client systems may include one or more client devices communicatively coupled to the ECG system, through a wired or wireless connection, or through a network, such as the Internet. In some embodiments, operation 508 includes transmitting the diagnosis to an email address, a URL, a client cloud storage account, a cloud service, or other client associated account.

Following operation 508, method 500 may end. In this way, method 500 may enable acquired ECG data to be automatically diagnosed using a hybrid ECG system, enabling rapid and accurate determination of a diagnosis, and wherein the diagnosis may be displayed to a user, such as a doctor or health care professional, and/or distributed to one or more client devices.

Figure 6:
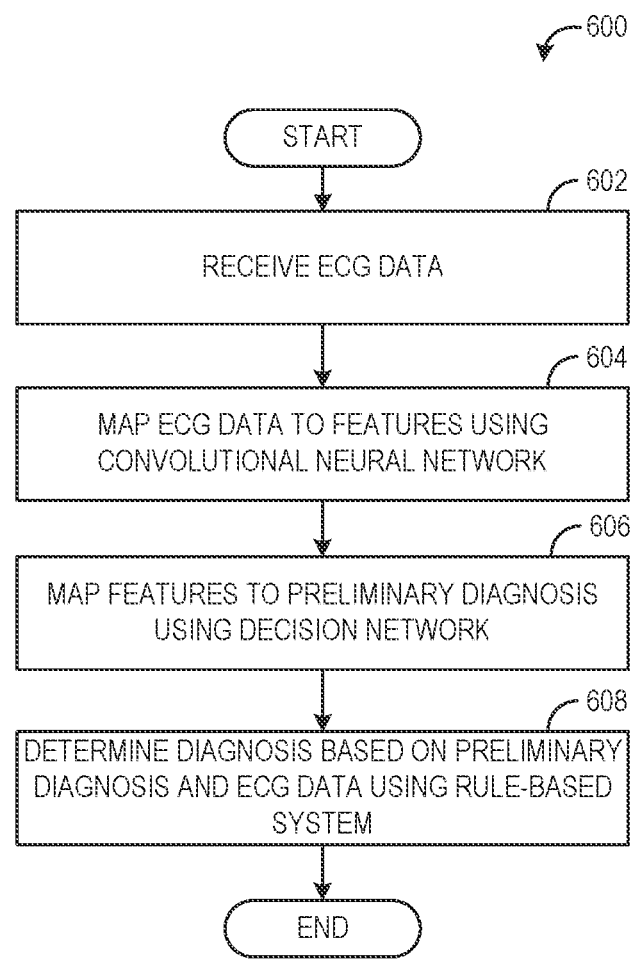
FIG. 6 is a flow chart illustrating a first embodiment of a method for automatically diagnosing ECG data using a hybrid ECG diagnostic system.

Turning to FIG. 6, a flow chart for a first embodiment of a method 600 for automatically determining a diagnosis for ECG data using a hybrid ECG diagnostic system is shown. Method 600 may be executed as part of method 500, as indicated at operation 504. In some embodiments, method 600 may be executed by hybrid ECG diagnostic system 200, implemented by one or more of ECG system 100, an edge device connected to ECG system 100, a cloud device in communication with ECG system 100, or any appropriate combination thereof. Method 600 may enable automatic, accurate, and use-case specific diagnosis of one or more ECGs for one or more patients.

Method 600 begins at 602, where acquired ECG data is received by a hybrid ECG diagnostic system, wherein the trained hybrid ECG diagnostic system comprises a rule-based system, such as rule-based system 204 described above, and a deep neural network, such as deep neural network 210 described above. The received ECG data includes one or more ECG waveforms/signals, indicating a heart's electrical activity through time. In some embodiments, the received ECG data may comprise data from a twelve lead ECG, as described in more detail above, with reference to FIG. 1. In some embodiments, the received ECG data may comprise data from a fifteen lead ECG. In some embodiments, the received ECG data may comprise data from a reduced lead ECG. In some embodiments, the received ECG data comprises 2D data of electrical potential through time, wherein electrical potential is plotted along the y-axis, and time is plotted along the x-axis. The received ECG data may be formatted as an SCP-ECG, a DICOM-ECG, a HL7 aECG, or other storage formats known in the art of ECGs.

At operation 604, the received ECG data is input into an input layer of a convolutional neural network of the deep neural network, and mapped to a plurality of features. Said another way, at operation 604, a convolutional neural network extracts one or more features from ECG data using one or more convolutional layers. The input layer of the convolutional neural network may comprise a plurality of neurons/input nodes, configured to receive the ECG data. In some embodiments, each neuron of the input layer of the convolutional neural network may be configured to receive a single value from the ECG data, wherein the single value may correspond to a pixel intensity value of an image of an ECG waveform. In some embodiments, the received ECG data may comprise a 2D data structure, such as a matrix or array, and a number of input neurons in an input layer of the convolutional neural network may be equal to the number of entries in the matrix/array, and further, the input neurons may be configured in a 2D arrangement reflecting the arrangement of the received 2D ECG data, thereby retaining the spatial relationships encoded within the 2D ECG data.

The convolutional neural network comprises one or more convolutional layers, including one or more filters in each convolutional layer. The filters comprise a plurality of weights, wherein each weight of a filter is used to compute a dot product with a corresponding value in either the received ECG data, or from a preceding feature map, the result of the dot product between the ECG data (or preceding feature map) is used to determine a current feature map. The filter weights are learned during a training phase, and are not hard-coded, thereby enabling the convolutional neural network to learn to identify different features correlated with diagnostic outcomes for different datasets/use-cases, even when those features may not appear intuitive to a human expert.

In each of the one or more convolutional layers, the one or more filters included in said layer are passed over each subregion of the received ECG data, wherein the size of the subregion is pre-determined, and the output of the filter applied to each subregion is used to produce a feature map. In some embodiments, a subregion may comprise a contiguous set of values from an image. In some embodiments, received ECG data comprises a 2D image of ECG waveforms, and a subregion comprises a pre-determined number of pixel intensity values from a spatially contiguous region within the 2D image.

A feature map comprises a plurality of values, indicating the extent of match between the one or more applied filters with each subregion of the received ECG data (or preceding feature map), thereby indicating a plurality of features present in the received ECG data. In some embodiments, a higher value in a subregion of a feature map indicates a greater extent of match between a given filter and a subregion of received ECG data corresponding to the subregion of the feature map. Said another way, a relatively high value in a feature map indicates a relatively high probability of a feature represented by a filter being present in the ECG data. Feature maps may comprise n dimensions (where n is a positive integer greater than 1), wherein n−1 dimensions of the feature map correspond to the dimensions of the input data, and wherein the $n^{th}$ dimension of the feature map is used for storing the result of each filter applied. In other words, the size of the $n^{th}$ dimension of a feature map corresponds to the number of filters applied to the input data.

Output from the convolutional neural network is produced by a plurality of neurons in an output layer of convolutional neural network, which receive as input an immediately preceding feature map. In some embodiments, the output from the convolutional neural network comprises one or more features present in the received ECG data. In some embodiments, output from the convolutional neural network comprises a feature map produced from the received ECG data using one or more convolutional layers.

At operation 606, the plurality of features produced by the convolutional neural network are input into a decision network of the deep neural network, and mapped to a preliminary diagnosis of the received ECG data. The decision network comprises an input layer comprising a plurality of neurons configured to receive output from the convolutional neural network, a plurality of fully/densely connected layers, and an output layer comprising a plurality of neurons configured to produce probability scores for each of a plurality of pre-determined diagnoses. In some embodiments, there may be an equal number of neurons of the input layer and outputs/features produced by the convolutional neural network, enabling a 1-to-1 correspondence between outputs from the convolutional neural network and the input neurons of the decision network. The decision network enables mapping of the plurality of features produced by the convolutional neural network to a preliminary diagnosis (comprising one or more diagnostic assessments), using a plurality of learned weights and biases.

At operation 608, the rule-based system, receives the preliminary diagnosis produced by the deep neural network, and the ECG data received at operation 602, and determines a diagnosis based thereon. In some embodiments, the preliminary diagnosis produced by the deep neural network may be used to adjust one or more criteria of the rule-based system. In some embodiments, the preliminary diagnosis may be used to select one or more types of pre-determined features for a feature extractor of the rule-based system to extract. In some embodiments, the preliminary diagnosis may be fed into a decision tree of the rule-based system along with the features extracted by the feature extractor, and used to determine a final diagnosis for the received ECG data. In some embodiments, the preliminary diagnosis produced by the deep neural network may be used to generate a confidence score for certain diagnosis, or multiple confidence scores for a multiple diagnosis, like both ventricular bundle brunch block and ischemia.

Following operation 608, method 600 may end. In this way, method 600 enables determination of a diagnosis for received ECG data using a hybrid system comprising a deep neural network and a rule-based system, wherein the ECG data is mapped to a preliminary diagnosis by the deep neural network, and the preliminary diagnosis along with the ECG data is used to determine a final diagnosis by the rule-based system. Thus, method 600 enables a diagnostic prediction of a rule-based system to be fine tuned using a preliminary diagnosis determined using an adaptable deep neural network, wherein the deep neural network may be trained on use-case specific data.

Figure 7:
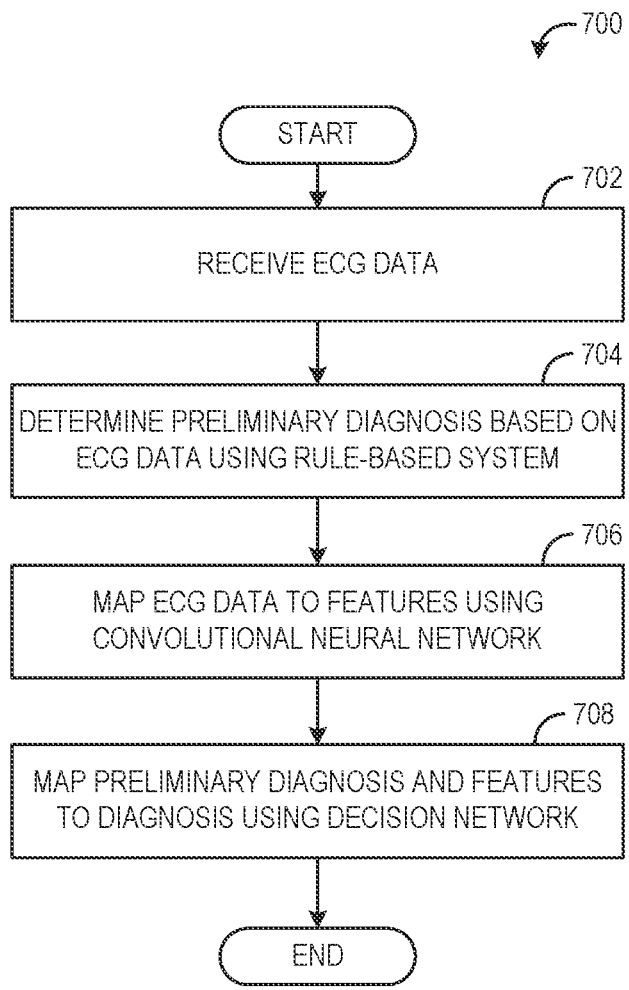
FIG. 7 is a flow chart illustrating a second embodiment of a method for automatically diagnosing ECG data using a hybrid ECG diagnostic system.

Turning to FIG. 7, a flow chart for a second embodiment of a method 700 for automatically determining a diagnosis for ECG data using a hybrid ECG diagnostic system is shown. Method 700 may be executed as part of method 500, as indicated at operation 504. In some embodiments, method 700 may be executed by hybrid ECG diagnostic system 300, implemented by one or more of ECG system 100, an edge device connected to ECG system 100, a cloud device in communication with ECG system 100, or any appropriate combination thereof. Method 700 may enable automatic, accurate, and use-case specific diagnosis of one or more ECGs for one or more patients.

Method 700 begins at 702, where acquired ECG data is received by a hybrid ECG diagnostic system, wherein the hybrid ECG diagnostic system comprises a rule-based system, such as rule-based system 304 described above, and a deep neural network, such as deep neural network 310 described above. The received ECG data includes one or more ECG waveforms/signals, indicating a heart's electrical activity through time. In some embodiments, the received ECG data may comprise data from a twelve lead ECG, as described in more detail above, with reference to FIG. 1. In some embodiments, the received ECG data may comprise data from a fifteen lead ECG. In some embodiments, the received ECG data may comprise data from a reduced lead ECG. In some embodiments, the received ECG data comprises 2D data of electrical potential through time, wherein electrical potential is plotted along the y-axis, and time is plotted along the x-axis. The received ECG data may be formatted as an SCP-ECG, a DICOM-ECG, a HL7 aECG, or other storage formats known in the art of ECGs.

At operation 704, the received ECG data is input into the rule-based system, and used by the rule-based system to determine a preliminary diagnosis. In some embodiments, inputting the received ECG data into the rule based system comprises inputting the received ECG data into a feature extractor of the rule-based system. In some embodiments, the feature extractor may perform one or more pre-processing operations on the input ECG data, prior to extracting features. The feature extractor may be configured as described above with reference to feature extractor 306, to determine one or more pre-determined features present in the received ECG data. In some embodiments, the pre-determined features may include one or more wave amplitudes, wave intervals/durations, and/or inter-wave intervals/durations.

The extracted features may be input into a decision tree, such as decision tree 308 described above. The decision tree may determine a path from a root node to a leaf node based on one or more decisions made at one or more decision nodes, wherein the decisions are based on hard-coded expert criteria for evaluating the one or more extracted features determined by the feature extractor. The leaf node may include one or more diagnostic assessments of the received ECG data, and may be used to determine a preliminary diagnosis for inputting into the decision network of the deep neural network.

At operation 706, the received ECG data is input into an input layer of a convolutional neural network, such as convolutional neural network 312, of the deep neural network, and mapped to a plurality of features. Said another way, at operation 706, a convolutional neural network extracts one or more features from ECG data using one or more convolutional layers. The input layer of the convolutional neural network may comprise a plurality of neurons configured to receive the ECG data. The convolutional neural network further comprises one or more convolutional layers, including one or more filters in each convolutional layer. Output from the convolutional neural network is produced by a plurality of neurons in an output layer of convolutional neural network. In some embodiments, the output from the convolutional neural network comprises one or more learned features present in the received ECG data. In some embodiments, learned features may comprise one or more wave characteristics, or conjunctions of wave characteristics. In some embodiments, output from the convolutional neural network comprises a feature map produced from the received ECG data using one or more convolutional layers.

At operation 708, the plurality of features output by the convolutional neural network are input into a decision network, such as decision network 314, of the deep neural network, along with the preliminary diagnosis determined by the rule-based system, and mapped to a final diagnosis of the received ECG data. The decision network comprises an input layer including a plurality of neurons configured to receive output from the convolutional neural network, and a preliminary diagnosis determined by the rule-based system. In some embodiments, the input layer of the decision network comprises a first plurality of neurons configured to receive the plurality of features output from the convolutional neural network, and a second plurality of neurons configured to receive the preliminary diagnosis determined by the rule-based system. The decision network further includes one or more fully/densely connected layers, and an output layer comprising a plurality of neurons configured to produce probability scores for each of a plurality of pre-determined diagnoses. The final diagnosis may be determined from the output of the decision network. In some embodiments, the decision network may output a probability score for each of a plurality of pre-determined diagnoses, wherein a probability score indicates a likelihood of an associated diagnosis, and the diagnosis (or diagnoses) selected as the final diagnosis may be selected based on associated probability scores.

Following operation 708, method 700 may end. The technical effect of determining a diagnosis for ECG data according to the method described in FIG. 7, is that a decision network may be informed of an initial/preliminary diagnosis determined based on expert criteria, which may afford a number of advantages, including a reduction in sensitivity of the decision network to variability in received ECG data. Specifically, the decision network may be made less sensitive to minor variations in ECG data by incorporating a second diagnostic prediction made using a distinct diagnostic approach.

Figure 8:
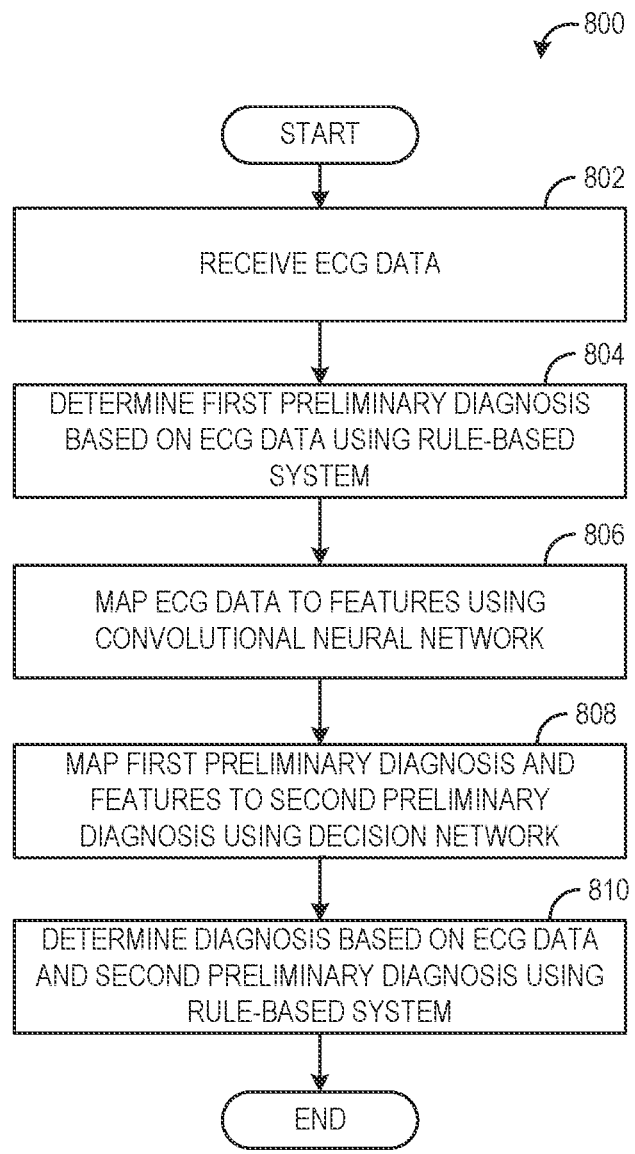
FIG. 8 is a flow chart illustrating a third embodiment of a method for automatically diagnosing ECG data using a hybrid ECG diagnostic system.

Turning to FIG. 8, a flow chart for a third embodiment of a method 800 for automatically determining a diagnosis for ECG data using a hybrid ECG diagnostic system is shown. Method 800 may be executed as part of method 500, as indicated at operation 504. In some embodiments, method 800 may be executed by hybrid ECG diagnostic system 400, implemented by one or more of ECG system 100, an edge device connected to ECG system 100, a cloud device in communication with ECG system 100, or any appropriate combination thereof. Method 800 may enable automatic, accurate, and use-case specific diagnosis of one or more ECGs for one or more patients.

Method 800 begins at 802, where acquired ECG data is received by a hybrid ECG diagnostic system, wherein the hybrid ECG diagnostic system comprises a rule-based system, such as rule-based system 404 described above, and a deep neural network, such as deep neural network 410 described above. The received ECG data includes one or more ECG waveforms/signals, indicating a heart's electrical activity through time. In some embodiments, the received ECG data may comprise data from a twelve lead ECG, as described in more detail above, with reference to FIG. 1. In some embodiments, the received ECG data may comprise data from a fifteen lead ECG. In some embodiments, the received ECG data may comprise data from a reduced lead ECG. In some embodiments, the received ECG data comprises 2D data of electrical potential through time, wherein electrical potential is plotted along the y-axis, and time is plotted along the x-axis. The received ECG data may be formatted as an SCP-ECG, a DICOM-ECG, a HL7 aECG, or other storage formats known in the art of ECGs.

At operation 804, the received ECG data is input into the rule-based system, and used by the rule-based system to determine a first preliminary diagnosis. In some embodiments, inputting the received ECG data into the rule based system comprises inputting the received ECG data into a feature extractor of the rule-based system. In some embodiments, the feature extractor may perform one or more pre-processing operations on the input ECG data, prior to extracting features. The feature extractor may be configured as described above with reference to feature extractor 406, to determine one or more pre-determined features present in the received ECG data. In some embodiments, the pre-determined features may include one or more wave amplitudes, wave intervals/durations, and/or inter-wave intervals/durations.

The extracted features may be input into a decision tree, such as decision tree 408 described above. The decision tree may determine a path from a root node to a leaf node based on one or more decisions made at one or more decision nodes, wherein the decisions are based on hard-coded expert criteria for evaluating the one or more extracted features determined by the feature extractor. The leaf node may include one or more diagnostic assessments of the received ECG data, and may be used to determine a preliminary diagnosis for inputting into the decision network of the deep neural network.

At operation 806, the received ECG data is input into an input layer of a convolutional neural network, such as convolutional neural network 412, of the deep neural network, and mapped to a plurality of features. Said another way, at operation 806, a convolutional neural network extracts one or more features from ECG data using one or more convolutional layers. The input layer of the convolutional neural network may comprise a plurality of neurons configured to receive the ECG data. The convolutional neural network further comprises one or more convolutional layers, including one or more filters in each convolutional layer. Output from the convolutional neural network is produced by a plurality of neurons in an output layer of convolutional neural network. In some embodiments, the output from the convolutional neural network comprises one or more learned features present in the received ECG data. In some embodiments, learned features may comprise one or more wave characteristics, or conjunctions of wave characteristics. In some embodiments, output from the convolutional neural network comprises a feature map produced from the received ECG data using one or more convolutional layers.

At operation 808, the plurality of features output by the convolutional neural network are input into a decision network, such as decision network 414, of the deep neural network, along with the first preliminary diagnosis determined by the rule-based system, and mapped to a second preliminary diagnosis of the received ECG data. The decision network comprises an input layer including a plurality of neurons configured to receive output from the convolutional neural network, and the first preliminary diagnosis determined by the rule-based system. In some embodiments, the input layer of the decision network comprises a first plurality of neurons configured to receive the plurality of features output from the convolutional neural network, and a second plurality of neurons configured to receive the first preliminary diagnosis determined by the rule-based system. The decision network further includes one or more fully/densely connected layers, and an output layer comprising a plurality of neurons configured to produce probability scores for each of a plurality of pre-determined diagnoses. The second preliminary diagnosis may be determined from the output of the decision network. In some embodiments, the decision network may output a probability score for each of a plurality of pre-determined diagnoses, wherein a probability score indicates a likelihood of an associated diagnosis, and the diagnosis (or diagnoses) selected as the second preliminary diagnosis may be selected based on associated probability scores.

At operation 810, the rule-based system, receives the second preliminary diagnosis produced by the deep neural network, and the ECG data received at operation 802, and determines a final diagnosis based thereon. In some embodiments, the second preliminary diagnosis produced by the deep neural network may be used to adjust one or more parameters of the rule-based system. In some embodiments, the preliminary diagnosis may be used to select one or more types of pre-determined features for the feature extractor of the rule-based system to extract. In some embodiments, the second preliminary diagnosis may be fed into a decision tree of the rule-based system along with the features extracted by the feature extractor, and used to determine a final diagnosis for the received ECG data.

Following operation 810, method 800 may end. In this way, method 800 employs a recursive diagnostic scheme, wherein a first preliminary diagnosis determined by a rule-based system may be mapped to a second preliminary diagnosis using a deep neural network. The second preliminary diagnosis is in turn used by the rule-based system to produce a final diagnosis. A technical effect of the above described recursive diagnostic scheme is that diagnostic accuracy, confidence, and consistency may be enhanced.

Figure 9:
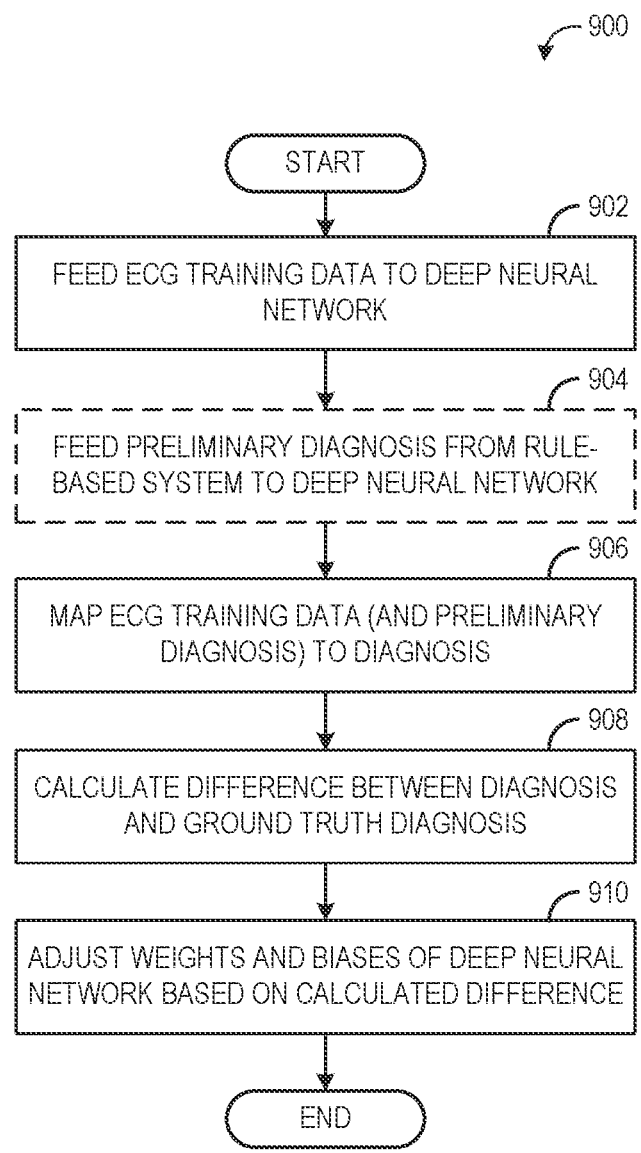
FIG. 9 is a flow chart illustrating a method for training a hybrid ECG diagnostic system to automatically diagnose ECG data, according to an exemplary embodiment.
Figure 10:
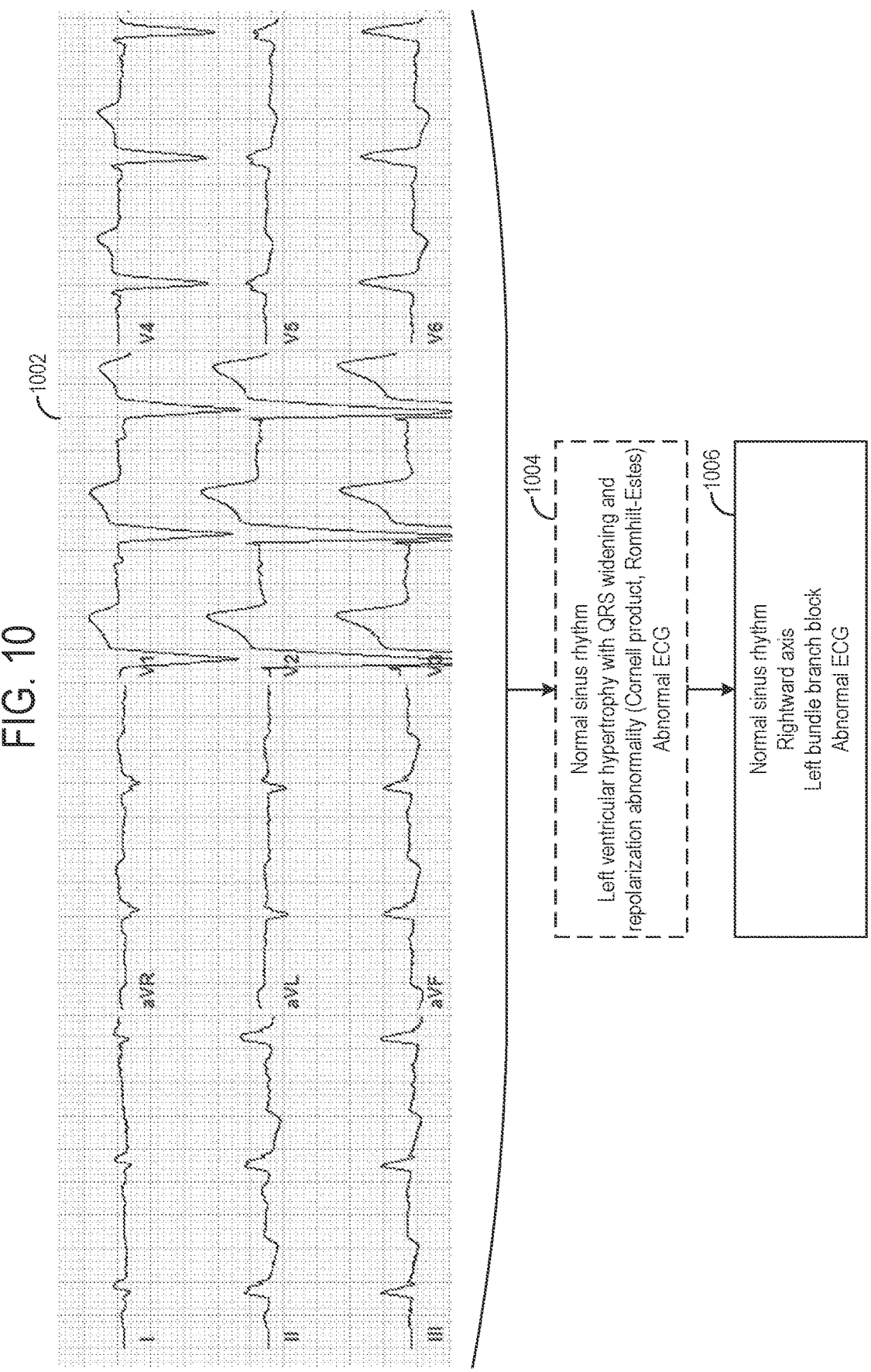
FIG. 10 shows an example ECG, a first diagnosis of the ECG produced by a rule-based system, and a second diagnosis of the ECG produced by a hybrid ECG diagnostic system, according to an exemplary embodiment of the current disclosure.

Referring to FIG. 9, a flow chart of a method 900 for training a deep neural network (such as deep neural networks 210, 310, and 410 shown in FIGS. 2, 3, and 4, respectively) is shown. Method 900 may be implemented by the ECG system 100 shown in FIG. 1. In some embodiments, method 900 may be implemented by deep neural network module 108, stored in non-transitory memory 106 of ECG processing system 102. Although both the convolutional neural network and decision network are herein trained simultaneously, and trained using a same training data set, it will be appreciated that the current disclosure provides for training the convolutional neural network and decision network separately, using distinct training data sets.

Method 900 begins at operation 902, where a training data pair, from a plurality of training data pairs, is fed to an input layer of a deep neural network, wherein the training data pair comprises ECG data and a corresponding ground truth diagnosis, and wherein the input layer of the deep neural network comprises an input layer of a convolutional neural network, coupled in series to a decision network. In some embodiments, the training data pair, and the plurality of training data pairs, may be stored in an ECG processing system, such as in ECG data module 112 in ECG processing system 102. In other embodiments, the training data pair may be obtained via communicative coupling between the ECG processing system and an external storage device, such as via Internet connection to a remote server. In some embodiments, the ground truth diagnoses are produced via expert analysis and/or via empirical analysis.

In some embodiments the training data pair is intelligently selected from stored ECG data, based on an intended use-case for the deep neural network. In some embodiments, the ECG training data pair fed to the deep neural network may comprise ECG data and a ground truth diagnosis determined for the ECG data, along with one or more pieces of metadata pertaining to the ECG training data pair. The metadata may include details regarding the ECG training data pair, such as one or more patient details (e.g., demographic details, health details, etc.), one or more ECG system details, one or more ECG conditions (e.g., resting ECG, exercise ECG, post infarction ECG), etc. The metadata may enable automatic and intelligent selection of training data pairs based on one or more details included therein, enabling training of a use-case specific deep neural network. In some embodiments, a deep neural network model for use in analyzing ECG data of elderly patients may be trained using training data pairs intelligently selected based on included metadata, wherein the included metadata indicates a patient's age is greater than a threshold age.

At operation 904, a preliminary diagnosis determined based on the ECG data by a rule-based system, such as rule-based systems 204, 304, and 404, described above may be fed to the deep neural network. In some embodiments, the preliminary diagnosis may be fed to an input layer of a decision network, coupled in series with the convolutional neural network, wherein the input layer of the decision network is further configured to receive a plurality of features determined by the convolutional neural network based on the ECG training data.

At operation 906, the deep neural network maps the input ECG data to a diagnosis by extracting a plurality of features from the ECG data by passing the ECG data through one or more convolutional layers of the convolutional neural network, and by mapping the plurality of features (and, in some embodiments, the preliminary diagnosis determined by the rule-based system) to a diagnosis using the decision network. In some embodiments the output of the deep neural network comprises a vector of probability scores, wherein each row of the vector corresponds to a pre-determined diagnosis, and wherein a probability score in a row corresponding to a pre-determined diagnosis indicates a likelihood of the pre-determined diagnosis applying to the ECG data.

At operation 908, the difference between the diagnosis produced by the deep neural network, and the ground truth diagnosis included within the ECG training data pair is calculated by the ECG processing system. In some embodiments, each diagnosis included within the ground truth diagnosis may have a ground truth probability score of one, while each diagnosis not included in the ground truth diagnosis may have a ground truth probability score of zero, and calculating the difference between the diagnosis produced by the deep neural network and the ground truth diagnosis may comprise calculating, for each diagnosis, a difference between a predicted probability score, and a ground truth probability score. In some embodiments, calculating the difference between the diagnosis and the ground truth diagnosis may include inputting the calculated difference into a loss function, wherein the loss function may include one or more mathematical operations performed on the calculated difference.

At operation 910, the weights and biases of the deep neural network are adjusted based on the difference calculated at operation 908. The difference may be back propagated through the layers of both the decision network and the convolutional network, starting from the output layer of the decision network, and proceeding back layer by layer to the input layer of the convolutional neural network. The weights and biases of each layer of the deep neural network may be adjusted based on the gradient (first partial derivative or approximation of the first partial derivative of the error function, with respect to the weight or bias being evaluated). Each weight (and bias) of the deep neural network may then be updated by adding the negative product of the gradient determined (or approximated) for the weight (or bias) with a predetermined step size. Method 900 may then end. It will be noted that method 900 may be repeated until the weights and biases of the deep neural network converge, the rate of change of the weights and/or biases of the deep neural network for each iteration of method 900 are below a threshold, or a validation error (determined using a validation data set, which is distinct from the training data set) below a pre-determined validation error threshold is obtained. Once a deep neural network is complete, it may be stored in non-transitory memory. In some embodiments, trained deep neural networks may be stored in a deep neural network library, such as deep neural network library module 180, shown in FIG. 1.

In this way, method 900 enables a hybrid ECG diagnostic system to learn a mapping from ECG data, to diagnoses, using intelligently selected ECG training data pairs. Method 900 may enable a hybrid ECG diagnostic system to more easily adapt to particular use-cases, by training on use-case specific data.

Turning to FIG. 10, an exemplary embodiment of ECG data 1002 (also referred to herein as electrocardiogram 1002) is shown, with a first diagnosis 1004 of ECG data 1002, produced by a rule-based system alone, and a second diagnosis 1006 of ECG data 1002, produced by a hybrid ECG diagnostic system according to an exemplary embodiment of the current disclosure. ECG data 1002 may be acquired by an ECG system, such as ECG system 100, using ten electrodes placed in electrical contact with a patient's skin. ECG data 1002 may be stored in non-transitory memory, such as in ECG data module 112. ECG data 1002 comprises a twelve lead ECG, including twelve distinct waveforms/signals measured concurrently for a same patient. Specifically, ECG data 1002 includes lead types I, II, III, aVR, aVL, aVF, V1, V2, V3, V4, V5, and V6, which may be measured using ten electrodes as described in more detail above with reference to FIG. 1.

Two exemplary embodiments of diagnoses are shown in FIG. 10, first diagnosis 1004, produced using a rule-based system without a deep neural network component, and second diagnosis 1006, produced using a hybrid ECG diagnostic system, such as hybrid ECG diagnostic systems 200, 300, and 400, discussed herein. First diagnosis 1004 includes a textual message indicating an assessment of the sinus rhythm, the QRS complex, and the overall normality/abnormality of ECG data 1002, as well as one or more physiological mechanisms underlying the indicated normality/abnormality. Likewise, second diagnosis 1006 includes a message, indicating a diagnostic assessment of the sinus rhythm, one or more physiological features of the heart, and the overall normality/abnormality of ECG 1002, as well as one or more physiological mechanisms underlying the indicated normality/abnormality. Second diagnosis 1006 correctly determines that ECG data 1002 indicates a rightward axis and left bundle branch block, whereas first diagnosis 1004 does not make this determination. Thus, an improvement in diagnostic accuracy of diagnoses determined via a hybrid ECG diagnostic system is demonstrated.

Turning to FIG. 11, an exemplary embodiment of a deep neural network library 1104 is shown. Deep neural network library 1104 may be stored in non-transitory memory of one or more computing systems. In one embodiment, deep neural network library 1104 may be stored in deep neural network library module 180 in non-transitory memory 106 of ECG processing system 102. Deep neural network library may be used in conjunction with one or more systems or methods described herein. In some embodiments, deep neural networks 210, 310, and 410, shown in hybrid ECG diagnostic systems 200, 300, and 400, respectively, may have been intelligently selected from a deep neural network library, such as deep neural network library 1104, based on the lead types present in the ECG data to be diagnosed. In some embodiments, in response to receiving reduced lead ECG data to diagnose, a hybrid ECG diagnostic system may automatically select a trained deep neural network from a deep neural network library, based on one or more metadata of the trained deep neural network. In one embodiment, in response to receiving twelve lead ECG data missing leads V1-V6, a deep neural network trained using ECG data missing leads V1-V6 may be selected from a deep neural network library. In this way, a hybrid ECG diagnostic system may determine a diagnosis for reduced lead ECG data, without simulating one or more missing leads.

Deep neural network library 1104 comprises a plurality of trained deep neural networks, including deep neural network 1110 and deep neural network 1130. In some embodiments, deep neural networks included in deep neural network library 1104 include parameters learned via training on reduced lead ECG data. Deep neural network library 1104 includes a plurality of trained deep neural networks, as indicated by the ellipsis between deep neural network 1110 and deep neural network 1130. In some embodiments, deep neural network library 1104 may include one or more trained deep neural networks for each reduced lead set permutation of a twelve lead ECG, wherein 4,094 reduced lead set permutations exist for a twelve lead ECG, and therefore, in some embodiments, 4,094 distinct, trained deep neural networks may be stored in deep library 1104. In some embodiments, deep neural network library 1104 may include one or more trained deep neural networks for each reduced lead set permutation of a fifteen lead ECG, wherein 32,766 reduced lead set permutations exist for a fifteen lead ECG. As used herein, a reduced lead set permutation comprises a distinct lead set produced for a set of n lead types, wherein each permutation may include between 1 and n−1 lead types (reduced lead sets comprising all missing leads, or no missing leads, are not included as these are trivial permutations).

Deep neural network 1110, which includes convolutional neural network 1112 and decision network 1114, arranged in series, may comprise a plurality of parameters (weights and biases) learned during a training process, such as method 1200 described below, using a first reduced lead set. Similarly, deep neural network 1130, including convolutional neural network 1132 and decision network 1134, may comprise a plurality of parameters learned during a training process using a second reduced lead set, wherein the first reduced lead set and second reduced lead set are different (that is, there is not a one-to-one correspondence between the lead types of the first reduced lead set and the lead types of the second reduced lead set). Deep neural network 1110 and deep neural network 1130 may be indexed according to one or more pieces of metadata, enabling rapid query and selection of a trained deep neural network based on received ECG data. In some embodiments, deep neural networks stored within deep neural network library 1104 may be indexed according to reduced lead set data on which they were trained, thus enabling automatic selection of a deep neural network based on received reduced lead ECG data.

In other words, by training a plurality of deep neural networks using different permutations of reduced lead sets, storing the trained deep neural networks in a deep neural network library according to the reduced lead ECG data on which the deep neural networks were trained, acquired ECG data with one or more missing leads may be efficiently and accurately mapped to a diagnosis by selecting a deep neural network from the deep neural network library trained on reduced lead ECG data missing the same type(s) of lead(s) as the acquired data.

Figure 12:
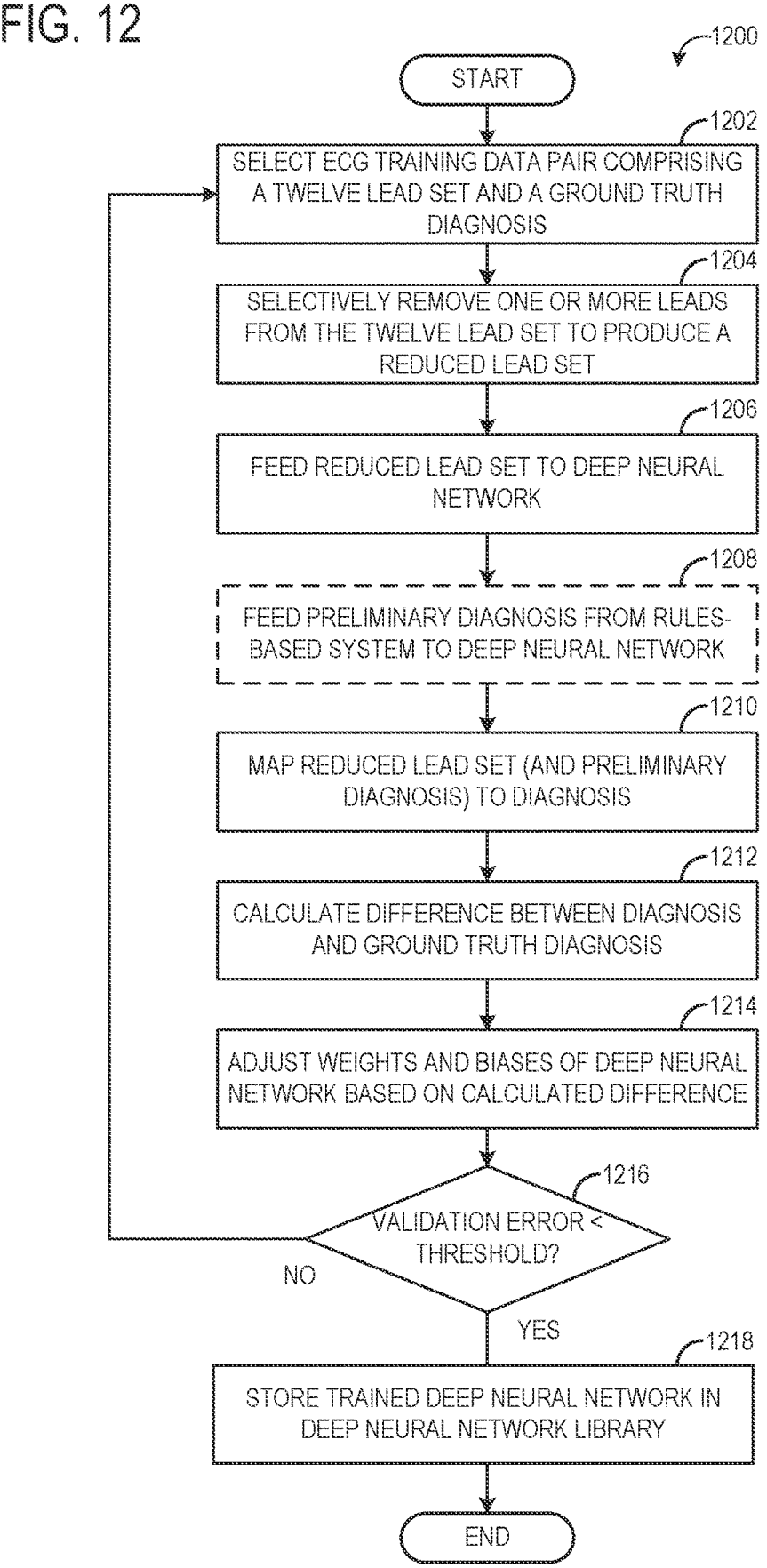
FIG. 12 is a flow chart illustrating a method for training a reduced lead ECG diagnostic system to automatically diagnose reduced lead ECG data, according to an exemplary embodiment.

Referring to FIG. 12, a flow chart of a method 1200 for training a deep neural network (such as deep neural networks 210, 310, and 410 shown in FIGS. 2, 3, and 4, respectively) to map reduced lead ECG data to diagnoses is shown. Method 1200 may be implemented by the ECG system 100 shown in FIG. 1. In some embodiments, method 1200 may be implemented by deep neural network module 108, stored in non-transitory memory 106 of ECG processing system 102. Although both the convolutional neural network and decision network are herein trained simultaneously, and trained using a same training data set, it will be appreciated that the current disclosure provides for training the convolutional neural network and decision network separately, using distinct training data sets.

Method 1200 begins at operation 1202, where an ECG training data pair comprising a twelve lead set and a corresponding ground truth diagnosis is selected. In some embodiments, the ECG training data pair may be selected from a plurality of training data pairs stored in non-transitory memory, such as in ECG data module 112 in ECG processing system 102. In other embodiments, the training data pair may be obtained via communicative coupling between the ECG system and an external storage device, such as via Internet connection to a remote server. In some embodiments, the ground truth diagnoses are produced via expert analysis and/or via empirical analysis.

In some embodiments the ECG training data pair is intelligently selected from stored ECG data, based on an intended use-case for the deep neural network. In some embodiments, the ECG training data may comprise twelve lead ECG data and a ground truth diagnosis determined for the twelve lead ECG data, along with one or more pieces of metadata pertaining to the ECG training data pair. The metadata may include details regarding the ECG training data pair, such as one or more patient details (e.g., demographic details, health details, etc.), one or more ECG system details/settings, one or more ECG conditions (e.g., resting ECG, exercise ECG, post infarction ECG), etc. The metadata may enable automatic and intelligent selection of ECG training data pairs based on one or more details included therein, enabling training of a use-case specific deep neural network.

At operation 1204, one or more leads are selectively removed from the twelve lead set to produce a reduced lead set. In some embodiments, the reduced lead set may comprise from one to eleven distinct lead types, that is, the twelve lead set comprises less than twelve leads and more than zero leads, each of a distinct lead type. In some embodiments, each ECG lead included in the ECG training data pair comprises an indication of lead type. In some embodiments, the number and type of leads to be removed may be selected by a user, or automatically determined according to a training routine.

At operation 1206, the reduced lead set is fed to the deep neural network. In some embodiments, at operation 1206 the reduced lead set, comprising less than twelve leads, is input into an input layer of a convolutional neural network, coupled in series to a decision network.

At operation 1208, a preliminary diagnosis determined based on the reduced lead ECG data by a rule-based system, such as rule-based systems 204, 304, and 404, described above, may be fed to the deep neural network. In some embodiments, the preliminary diagnosis may be fed to an input layer of a decision network, coupled in series with the convolutional neural network, wherein the input layer of the decision network is further configured to receive a plurality of features determined by the convolutional neural network based on the ECG training data.

At operation 1208, the deep neural network maps the reduced lead set to a diagnosis by passing the ECG data through one or more convolutional layers of the convolutional neural network, to extract a plurality of features from the reduced lead set, and by mapping the plurality of extracted features (and, in some embodiments, the preliminary diagnosis determined by the rule-based system) to a diagnosis using the decision network. In some embodiments the output of the deep neural network comprises a vector of probability scores, wherein each row of the vector corresponds to a pre-determined diagnosis, and wherein a probability score in a row corresponding to a pre-determined diagnosis indicates a likelihood of the pre-determined diagnosis applying to the reduced lead set.

At operation 1212, the difference between the diagnosis produced by the deep neural network, and the ground truth diagnosis included within the ECG training data pair is calculated. In some embodiments, each diagnosis included within the ground truth diagnosis may have a ground truth probability score of one, while each diagnosis not included in the ground truth diagnosis may have a ground truth probability score of zero, and calculating the difference between the diagnosis produced by the deep neural network and the ground truth diagnosis may comprise calculating, for each diagnosis, a difference between a predicted probability score, and a ground truth probability score. In some embodiments, calculating the difference between the diagnosis and the ground truth diagnosis may include using a loss function, wherein the loss function may include one or more mathematical operations performed on the diagnosis and the ground truth diagnosis.

At operation 1214, the weights and biases of the deep neural network are adjusted based on the difference calculated at operation 1212. The difference may be back propagated through the layers of both the decision network and the convolutional neural network, starting from the output layer of the decision network, and proceeding back layer by layer to the input layer of the convolutional neural network. The weights and biases of each layer of the deep neural network may be adjusted based on the gradient (first partial derivative or approximation of the first partial derivative of the calculated error, with respect to the weight or bias being evaluated). Each weight (and bias) of the deep neural network may then be updated by subtracting the product of the gradient (determined or approximated for the weight or bias being adjusted) multiplied by a predetermined step size.

At operation 1216, the ECG processing system may determine if the validation error of the deep neural network is below a threshold. The validation error may be determined using a validation data set, comprising a plurality of reduced lead sets and corresponding ground truth diagnoses, wherein the data included in the validation data set is distinct from the data included in the training data set. The validation error may be determined by calculating a difference between a plurality of diagnosis predicted by the deep neural network based on the validation data, and a corresponding plurality of ground truth diagnosis, in substantially the same manner as described above, in regards to operation 1212. If at operation 1216, it is determined that the validation error is not less than the threshold, method 1200 proceeds to operation 1202, wherein a new ECG training data pair is selected, and operations 1204-1216 are executed on the new ECG training data pair.

However, if at 1216, the ECG processing system determines that the validation error of the deep neural network is below the threshold, method 1200 proceeds to operation 1218, which includes storing the trained deep neural network in a deep neural network library, such as deep neural network library 1104 shown in FIG. 11. In some embodiments, storing the trained deep neural network in the deep neural network library comprises indexing the trained deep neural network using one or more pieces of metadata, wherein metadata may include the type(s) of ECG leads present in the reduced lead sets used to train the deep neural network. The technical effect of indexing stored, trained deep neural networks based on lead types present in the reduced lead sets used during a training phase of the deep neural network, is that an ECG processing system may rapidly query and select a trained deep neural network for use in a hybrid ECG diagnostic system, wherein the hybrid ECG diagnostic system is to be used in diagnosing reduced lead ECG data comprising a same reduced lead set as the selected trained deep neural network. Following operation 1218, method 1200 may end.

Figure 13:
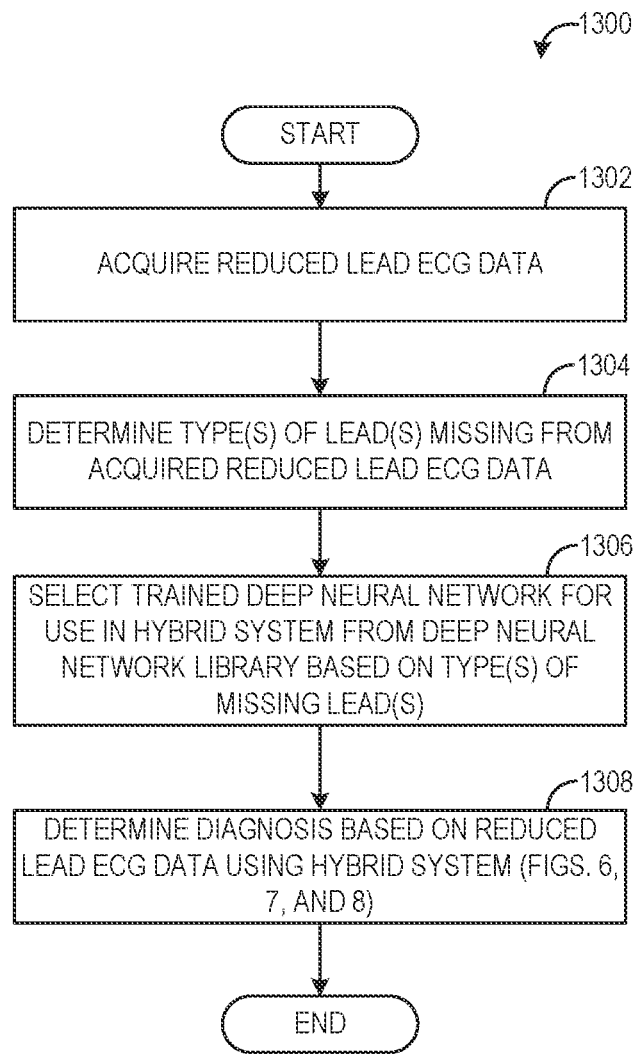
FIG. 13 is a flow chart illustrating a method for diagnosing reduced lead ECG data using a reduced lead ECG diagnostic system.

Turning to FIG. 13, a flow chart of an exemplary method 1300 for diagnosing reduced lead ECG data using a hybrid ECG diagnostic system is shown. In some embodiments, method 1300 may be executed by ECG system 100, an edge device connected to ECG system 100, a cloud device in communication with ECG system 100, or any appropriate combination thereof. Method 1300 may enable automatic, accurate, and use-case specific diagnosis of one or more reduced lead ECGs for one or more patients.

Method 1300 begins at operation 1302, where reduced lead ECG data is acquired by an ECG system. Reduced lead ECG data may comprise one or more lead signals/waveforms indicating an electrical activity of a heart through time. Reduced lead ECG data may be missing one or more lead signals. In some embodiments, reduced lead ECG data may comprise less than twelve leads, and more than zero leads. In some embodiments, acquiring reduced lead ECG data may comprise measuring the less than twelve leads using less than ten electrodes in electrical contact with a patient, as described in more detail above, with reference to FIG. 1. Acquired ECG data may be stored in memory for later processing. In some embodiments, the reduced lead ECG data acquired at operation 1302 comprises 2D data of electrical potential through time, wherein electrical potential is plotted along the y-axis, and time is plotted along the x-axis. Reduced lead ECG data acquired at operation 1302 may be stored in one or more formats, including SCP-ECG, DICOM-ECG, HL7 aECG, and other storage formats known in the art of ECGs. Acquisition of reduced lead ECG data at operation 1302 may occur under various conditions, such as when the patient is resting, during exercise, or in an ambulance.

At operation 1304, the type(s) of leads missing from the acquired reduced lead ECG data is determined. In some embodiments, each ECG lead included in the reduced lead ECG data may include a lead type identifier, wherein the lead type identifier may comprise a piece of metadata associated with the reduced lead ECG data. Determining the missing lead types may comprise comparing the lead type identifiers included within the reduced lead ECG data against a standard lead type set. In some embodiments, determining which lead types are missing from acquired reduced lead ECG data may comprise comparing a set of lead type identifiers for the reduced lead ECG data against a standard twelve lead set. In some embodiments, determining which lead types are missing from acquired reduced lead ECG data may comprise comparing a set of lead type identifiers for the reduced lead ECG data against a standard fifteen lead set.

At operation 1306, a deep neural network is selected from a deep neural network library, for use in diagnosing the reduced lead ECG data based on the type(s) of missing lead(s) determined at operation 1304. The deep neural network selected may be used in a hybrid ECG diagnostic system, such as those described above with reference to FIGS. 2, 3, 4, to automatically determine a diagnosis for the acquired reduced lead ECG data. In some embodiments, selecting the trained deep neural network from the deep neural network library comprises querying the deep neural network library using the one or more missing lead types determined for the reduced lead ECG data, and selecting a deep neural network based on the ECG lead types missing from the reduced lead ECG data matching the lead types missing from the ECG training data used to train the deep neural network. In some embodiments, selecting the trained deep neural network from the deep neural network library comprises querying the deep neural network library using the one or more leads included within the reduced lead ECG data, and selecting a deep neural network based on the lead types present in the acquired reduced lead ECG data matching the lead types present in the ECG training data used to train the deep neural network. The deep neural networks within the deep neural network library may be indexed based on one or more attributes of the ECG training data used during a training phase. In one embodiment, the deep neural networks within the deep neural network library may be indexed based on the lead types present (and/or missing) from the ECG training data used during a training phase. By selecting a deep neural network trained using a same reduced lead set as the acquired reduced lead ECG data, a more accurate and consistent diagnosis may be made, without simulating the one or more missing leads.

At operation 1308, a diagnosis is determined for the reduced lead ECG data acquired at operation 1302 using one or more of hybrid ECG diagnostic systems 200, 300, and/or 400, employing the deep neural network selected at operation 1306. The hybrid ECG diagnostic system may determine the diagnosis for the reduced lead ECG data using one or more of the steps of methods 600, 700, and 800, described above in more detail. In a first exemplary embodiment, operation 1308 comprises hybrid ECG diagnostic system 200 executing one or more operations of method 600, to determine a diagnosis based on acquired ECG data. In a second exemplary embodiment, operation 1308 comprises hybrid ECG diagnostic system 300 executing one or more operations of method 700, to determine a diagnosis based on acquired ECG data. In a third embodiment, operation 1308 comprises hybrid ECG diagnostic system 400 executing one or more operations of method 800, to determine a diagnosis based on acquired ECG data. In some embodiments, the ECG system executing method 1300 may select between the first, second, and third embodiments of a hybrid ECG diagnostic system based on one or more features of the acquired ECG data.

In this way, method 1300 enables rapid, accurate, and computationally efficient mapping of an acquired reduced lead ECG to a diagnosis, using a hybrid diagnostic system, by intelligently selecting a deep neural network from a deep neural network library based on the one or more lead types missing from the acquired reduced lead ECG data, and incorporating the selected deep neural network into the hybrid ECG diagnostic system.

When introducing elements of various embodiments of the present disclosure, the articles "a," "an," and "the" are intended to mean that there are one or more of the elements. The terms "first," "second," and the like, do not denote any order, quantity, or importance, but rather are used to distinguish one element from another. The terms "comprising," "including," and "having" are intended to be inclusive and mean that there may be additional elements other than the listed elements. As the terms "connected to," "coupled to," etc. are used herein, one object (e.g., a material, element, structure, member, etc.) can be connected to or coupled to another object regardless of whether the one object is directly connected or coupled to the other object or whether there are one or more intervening objects between the one object and the other object. In addition, it should be understood that references to "one embodiment" or "an embodiment" of the present disclosure are not intended to be interpreted as excluding the existence of additional embodiments that also incorporate the recited features.

In addition to any previously indicated modification, numerous other variations and alternative arrangements may be devised by those skilled in the art without departing from the spirit and scope of this description, and appended claims are intended to cover such modifications and arrangements. Thus, while the information has been described above with particularity and detail in connection with what is presently deemed to be the most practical and preferred aspects, it will be apparent to those of ordinary skill in the art that numerous modifications, including, but not limited to, form, function, manner of operation and use may be made without departing from the principles and concepts set forth herein. Also, as used herein, the examples and embodiments, in all respects, are meant to be illustrative only and should not be construed to be limiting in any manner.

The invention claimed is:

1. A method comprising:
  acquiring reduced lead electrocardiogramata), wherein the reduced lead ECG data comprises less than twelve lead signals;
  determining a type of each of the less than twelve lead signals;
  selecting a deep neural network from among a plurality of deep neural networks based on the type of each of the less than twelve lead signals; and
  mapping the less than twelve lead signals to a diagnosis using the deep neural network.

2. The method of claim 1, wherein the type of each of the less than twelve lead signals is one of I, II, III, aVR, aVL, aVF, V1, V2, V3, V4, V5, and V6, and wherein the type of each of the less than twelve lead signals is distinct from each other type of the less than twelve lead signals.

3. The method of claim 1, wherein the selecting the deep neural network from among a plurality of deep neural networks comprises selecting the deep neural network from a deep neural network library comprising the plurality of deep neural networks.

4. The method of claim 3, wherein mapping the less than twelve lead signals to the diagnosis using the deep neural network comprises:
  mapping the less than twelve lead signals to a plurality of features using the convolutional neural network; and
  mapping the plurality of features from the convolutional neural network to the diagnosis using the decision network.

5. The method of claim 4, the method further comprising:
  determining a preliminary diagnosis based on the less than twelve lead signals using a rule-based system, and wherein mapping the plurality of features from the convolutional neural network to the diagnosis using the decision network further comprises:
  inputting the preliminary diagnosis into an input layer of the decision network; and
  mapping both the preliminary diagnosis and the plurality of features to the diagnosis using the decision network.

6. The method of claim 1, wherein the deep neural network is stored in a deep neural network library and indexed based on a training data set used to train the deep neural network.

7. The method of claim 6, wherein selecting the deep neural network based on the type of each of the less than twelve lead signals comprises matching the type of each of the less than twelve lead signals with an index of the deep neural network, wherein the index indicates lead signal types used to train the deep neural network.

8. The method of claim 1, wherein acquiring reduced lead ECG data comprises measuring the less than twelve lead signals using less than 10 electrodes.

9. A method for training a deep neural network to automatically diagnose reduced lead electrocardiograms (ECGs), the method comprising:
  selecting an ECG training data pair comprising a lead signal set and a ground truth diagnosis corresponding to the lead signal set;
  selectively removing one or more lead signals from the lead signal set to produce a reduced lead signal set;
  feeding the reduced lead signal set to the deep neural network, the deep neural being network configured to output a diagnosis based on the reduced lead signal set to a diagnosis;
  calculating a difference between the diagnosis and the ground truth diagnosis; and
  adjusting one or more parameters of the deep neural network based on the calculated difference.

10. The method of claim 9, the method further comprising:
  determining a validation error of the deep neural network; and
  responding to the validation error being below a predetermined threshold by:
    storing the deep neural network in a deep neural network library; and
    indexing the deep neural network in the deep neural network library based on the removed one or more lead signals.

11. The method of claim 9, wherein the lead signal set is a twelve lead electrocardiogram of a patient, and wherein the ground truth diagnosis corresponding to the lead signal set comprises an expert generated diagnosis determined for the patient.

12. The method of claim 9, wherein adjusting one or more parameters of the deep neural network based on the calculated difference comprises, performing backpropagation using the calculated difference to adjust a plurality of weights and/or a plurality of biases of the deep neural network.

13. The method of claim 9, wherein the deep neural network comprises a convolutional neural network coupled in series to a decision network, and wherein mapping the reduced lead signal set to the diagnosis comprises:
    mapping the reduced lead signal set to a plurality of features using the convolutional neural network; and
    mapping the plurality of features from the convolutional neural network to the diagnosis using the decision network.

14. The method of claim 13, the method further comprising:
    determining a preliminary diagnosis based on the reduced lead signal set using a rule-based system, and wherein mapping the plurality of features from the convolutional neural network to the diagnosis using the decision network further comprises:
        inputting the preliminary diagnosis into an input layer of the decision network; and
        mapping the preliminary diagnosis and the plurality of features to the diagnosis using the decision network.

15. An electrocardiogram (ECG) processing system comprising:
    a display device;
    a memory storing a deep neural network library comprising a plurality of trained deep neural networks, and instructions; and
    a processor communicably coupled to the memory and the display device and when executing the instructions, configured to:
        acquire reduced lead ECG data, wherein the reduced lead ECG data comprises less than twelve lead signals;
        select a deep neural network from the deep neural network library based on the less than twelve lead signals;
        map the less than twelve lead signals to a diagnosis using the deep neural network; and
        display the diagnosis via the display device.

16. The system of claim 15, the system further comprising less than 10 electrodes, and wherein the system is configured to acquire reduced lead ECG data using the less than 10 electrodes.

17. The system of claim 15, wherein the deep neural network comprises a convolutional neural network and a decision network.

18. The system of claim 15, wherein the processor is configured to map the less than twelve lead signals to the diagnosis using the deep neural network by:
    mapping the less than twelve lead signals to a plurality of features using the convolutional neural network; and
    mapping the plurality of features from the convolutional neural network to the diagnosis using the decision network.

19. The system of claim 15, wherein the memory further comprises a rule-based ECG diagnostic system, and wherein the processor is further configured to map the less than twelve lead signals to the diagnosis using the deep neural network by:
    mapping the less than twelve lead signals to a plurality of features using the convolutional neural network;
    determining a preliminary diagnosis based on the less than twelve lead signals using the rule-based ECG diagnostic system; and
    mapping both the preliminary diagnosis and the plurality of features to the diagnosis using the decision network.

20. The system of claim 15, wherein the deep neural network library comprises from 1 to 4,094 trained deep neural networks, wherein each of the trained deep neural networks comprises parameters learned via training on training data comprising distinct reduced ECG lead sets.

\* \* \* \* \*